(12) United States Patent
Adamis

(10) Patent No.: US 6,524,581 B1
(45) Date of Patent: Feb. 25, 2003

(54) PREVENTION AND TREATMENT OF RETINAL ISCHEMIA AND EDEMA

(75) Inventor: Anthony P. Adamis, Jamaica Plain, MA (US)

(73) Assignee: The Children's Medical Center Corporation, Boston, MA (US)

(*) Notice: Subject to any disclaimer, the term of this patent is extended or adjusted under 35 U.S.C. 154(b) by 0 days.

(21) Appl. No.: 09/474,523

(22) Filed: Dec. 29, 1999

Related U.S. Application Data

(63) Continuation-in-part of application No. 09/248,752, filed on Feb. 12, 1999.
(60) Provisional application No. 60/114,221, filed on Dec. 30, 1998.

(51) Int. Cl.$^7$ .................. A61K 39/395; C07K 16/00
(52) U.S. Cl. .................. 424/130.1; 530/387.1
(58) Field of Search .................. 435/6, 7.1, 69.1, 435/91.1, 440, 325, 352, 353, 366, 368, 371, 372, 375, 320.1; 530/387.1, 388.1, 388.2; 514/44; 424/130.1, 133.1, 145.1, 152.1; 536/23.1, 24.31, 24.5

(56) References Cited

U.S. PATENT DOCUMENTS

| | | |
|---|---|---|
| 5,597,567 A | 1/1997 | Whitcup et al. |
| 5,814,500 A | 9/1998 | Dietz |
| 5,821,341 A | 10/1998 | McClelland et al. |
| 5,831,029 A | * 11/1998 | Gallatin et al. |

FOREIGN PATENT DOCUMENTS

| | | |
|---|---|---|
| EP | 0 314 863 A | 5/1989 |
| EP | 0 512 301 A1 | 11/1992 |
| EP | 0 528 931 B1 | 7/1998 |
| WO | WO 91/16927 | 11/1991 |
| WO | WO 93/06864 A | 4/1993 |
| WO | WO 98/24797 | 6/1998 |
| WO | WO 98/46264 A | 10/1998 |
| WO | WO 99/45920 | 9/1999 |

OTHER PUBLICATIONS

Branch, A.D. TIBS, vol. 23, Feb. 1998, pp. 45–50.*
Jen et al., Stem Cells 2000; 18:307–319.*
Green et al., J. A. Coll. Surg., (Jul. 2000).*
Kleinberg et al., Am. J. Health-Syst. Pharm., vol. 52, pp. 1323–1336 (Jun., 1995).*
Yagi et al., Diabetes, vol. 44, No. 7, pp. 744–752 (Jul. 1995).*
Rao et al., Alterations in Stimulus–Induced Integrin Expression in Peripheral Blood Neutrophils of Patients With Diabetic Retinopathy, The American Journal of the Medical Sciences, Mar. 1997, vol. 313, No. 3, pp. 131–137.*
Hamada K, et al., "Involvement of Mac–1–mediated Adherence and Sphingosine 1–phosphate in Survival of Phorbol Eser–treated U937 Cells," *Biochemical and Biophysical Research Communications*, 244(3): 745–750 (1998).
Kelly, T.A., et al., "Cutting Edge: a Small Molecule Antagonist of Lfa–1–mediated Cell Adhesion," *J. Immunology*, 163(10): 5173–5177 (1999).
Shannon, J.P., et al., "Novel cyclic peptide inhibits intercellular adhesion molecule–1–mediated cell aggregation," *Journal of Peptide Research*, 58(2): 140–150 (2001).
Zhu, G.D., et al., "Selective Inhibition of Icam–1 and E–selectin Expression in Human Endothelial Cells. 2. Aryl Modifications of 4–(Aryloxy) Thieno[2,3–c]pyridines with Fine–tuning at C–2 Carbamides," *Journal of Medicinal Chemistry*, 44(21): 3469–3487 (2001).
Cohen Tervaert, J.W., et al., "Novel Therapies for Anti–neutrophil Cytoplasmic Antibody–associated Vasculitis," *Current Opinion in Nephrology and Hypertension*, 10(2): 211–217 (2001).
Dragun, D. and Haller, H., "Diapedesis of Leukocytes: Antisense Oligonucleotides for Rescue," *Experimental Nephrology*, 7(2): 185–192 (1999).
Tsuji, T. et al., "Integrin B2 (Cd18)–mediated Cell Proliferation of HEL Cells of a Hematopoietic–supportive Bone Marrow Stromal Cell Line, Hes 5 Cells," *Blood*, 91(4) 1263–1271 (1998).
Nathan,D.M., "The Pathophysiology of Diabetic Complications: How Much Does the Glucose Hypothesis Explain?," *Annual Intern Medicine*, 123(1Pt 2): 86–89 (1996).
Porta, M., "Diabetic Retinopathy and Metabolic Control," *European Journal of Ophthalmology*, 3(4): 207–215 (1993).
Lightman, S., "Does Aldose Reductase Have a Role in the Development of the Ocular Complications of Diabetes?," *Eye*, 7(Pt 2): 238–241 (1993).
Frank, R.N., "On the Pathogenesis of Diabetic Retinopathy. A 1990 Update," *Ophthalmology*, 98(5): 586–593 (1991).
Wiedemann, P., "What Is Th Etiology of Diabetic Retinopathy?," *Ophthalmologe*, 90(5): 426–433 (1993).
Kessler, L, et al., "Von Willebrand Factor in Diabetic Angiopathy," *Diabetes Metabolism* , 24(4): 327–336 (1998).
Ways, D.K., and Sheetz, M.J., "The Role of Protein Kinase C in the Development of the Complications of Diabetes," *Vitamin Hormone*, 60: 149–193 (2000).
Antonetti, D.A., et al., "Molecular Mechanisms of Vascular Permeability in Diabetic Retinopathy," *Seminar of Ophthalmology*, 14(4): 240–248 (1999).

(List continued on next page.)

*Primary Examiner*—Andrew Wang
*Assistant Examiner*—James S. Schultz
(74) *Attorney, Agent, or Firm*—Hamilton, Brook, Smith & Reynolds, P.C.

(57) ABSTRACT

The present invention relates to methods of treating retinopathy, retinal ischemia and/or retinal edema comprising administering an integrin or integrin subunit antagonist, leukocyte adhesion-inducing cytokine antagonist or growth factor antagonist, a selectin antagonist or adhesion molecule antagonist.

26 Claims, 16 Drawing Sheets

OTHER PUBLICATIONS

Ambati, J., et al., "Transscleral Delivery of Bioactive Protein to the Choroid and Retina," *Investigative Ophthalmology & Visual Science*, 41(5): 1186–1191 (2000).

Henry, S.P., et al., "Antiviral Activity and Ocular Kinetics of Antisense Oligonucleotides Designed to Inhibit Cmv Replication," *Investigative Ophthalmology & Visual Science*, 42(11): 2646–2651 (2000).

Olson, J. A. et al., "Soluble leucocyte adhesion molecules in diabetic retinopathy stimulate retinal capillary endothelial cell migration," *Diabetolgia*, 40(10):1166–71 (Oct. 1997).

Uchio E. et al., "Suppression of experimental uveitis with monoclonal antibodies to ICAM–1 and LFA–1, " *Investigative Ophthalmology and Visual Science*, 35(5):2626–31 (Apr. 1994).

Henley W. L. et al., "Leukocyte migration inhibition in chronic ophthalmic disorders. 5. Diabetic retinopathy and the effect of photocoagulation," *American Journal of Ophthalmology*, 76(2):279–83 (Aug. 1973).

Barouch F. C. et al., "Integrin–mediated neutropil adhesion and retinal leukostasis in diabetes," *Investigative Ophthalmology and Visual Science*, 41(5):1153–8 (Apr. 2000).

Ambati, J., et al., *IOVS*, 41(5):1186–1191 (2000).

Lawrence M. B. et al., "Leukocytes Roll on a Selectin at Physiologic Flow Rates: Distinction from and Prerequisite for Adhesion Through Integrins," *Cell*, vol. 65:859–873 (1991).

Arnold, T. et al., "Increased PMN Adherence on Endothelial Cells After Hypoxia: Involvement of PAF, CD18/CD11b, and ICAM–1," *American Physiological Society* C1102–C1110 (1993).

Springer, T. A., "Traffic Signals for Lymphocyte Recirculation and Leukocyte Emigration: The Multistep Paradigm," *Cell*, vol. 76:301–314 (1994).

Schmid–Schönbein, G.W., "Granulocyte Activation and Capillary Obstruction," Liepshc DW (ed): Blood Flow in Large Arteries: Applications to Atherogenesis and Clinical Medicine. Monogr Atheroscler, Basel, Karger, vol. 15:150–159 (1990).

Panès, J. et al., "Diabetes Exacerbates Inflammatory Responses to Ischemia–Reperfusion," *Circulation*, vol. 93:161–167(1996).

Lu, M. et al., "VEGF Increases Retinal Vascular ICAM–1 Expression and Neutrophil Adhesion to Endothelial Cells," *IOVS*, vol. 39(4) (1998) (Abstract).

Limb, G. A. et al., "Evidence of Chronic Inflammation in Retina Excised After Relaxing Retinotomy for Anterior Proliferative Vitreoretinopathy," *Graefe's Arch Clin. Exp. Ophthalmol*, vol. 234:213–220 (1996).

Douglas, J. T. et al., "Vascular and Platelet Adhesion Molecules: E–Selectin, ICAM–1, VCAM–1, GMP–140 and Platelet Derived Growth Factor in Diabetes," (Abstract), Fibrinolysis, 8 (Suppl. 1): 132 (1994).

Lisby, S. et al., "Intercellular Adhesion Molecule–I (ICAM–I) Expression Correlated to Inflammation," *British Journal of Dermatology*, vol. 120:479–484 (1989).

Ashton, N. "Pathogenesis of Diabetic Retinopathy," edited by H.L. Little, et al., New York, Thieme Stratton (1983) *Diabetic Retinopathy* 85–106.

Chakrabarti, D. et al., "IFN–α Induces Autoimmune T Cells Through the Induction of Intracellular Adehesion Molecule–1 and B7.2," *J. of Immunol.* vol. 157:522–528 (1996).

Lampeter, E. R. et al., "Elevated Levels of Circulating Adhesion Molecules in IDDM Patients and in Subjects at Risk for IDDM," *Diabetes* vol. 41:1668–1671 (1992).

Heidenkummer, H. et al., "Intercellular Adhesion Molecule–1 (ICAM–1) and Leukocyte Function–Associated Antigen–1 (LFA–1) Expression in Human Epiretinal Membranes," *Graefe's Arch. Clin. Exp. Ophthalmol.* vol. 230:483–487 (1992).

Albertini, J. P. et al., "Are Soluble Adhesion Glycoproteins a Marker for Coronary Lesions in the Diabetic Patient?," (Abstract No. 1561) Abstracts of the 16th International Diabetes Federal Congress, Diabetologia, vol. 40, Suppl. 1, (Jun., 1997).

Schmid–SchönBein, G.W., "The Damaging Potential of Leukocyte Activation in the Microcirculation," *Angiology— The Journal of Vascular Diseases* 45–56 (1993).

Roep, B. O. et al., "Soluble Forms of Intercellular Adhesion Molecule–1 in Insulin–Dependent Diabetes Mellitus," *The Lancet*, vol. 343:1590–1593 (1994).

Kohner, E.M. et al., *Diabetic Retinopathy* 25:1985–1102 (1975).

Schröder, S. et al., "Activated Monocytes and Granulocytes, Capillary Nonperfusion, and Neovascularization in Diabetic Retinopathy," *American Journal of Pathology*, vol. 139(1):81–100 (1991).

McLeod, S. D. et al., "Enhanced Expression of Intracellular Adhesion Molecule–1 and P–Selectin in the Diabetic Human Retina and Choroid," *American Journal of Pathology*, vol. 147(3):642–653 (1995).

Larson, R. S. et al., "Structure and Function of Leukocyte Integrins," *Immunological Reviews*, vol. 114:181–217 (1990).

De Mesmaeker, A. et al., "Antisense Oligonucleotides," *Acc. Chem. Res.*, vol. 28:366–374 (1995).

Setlow, J. K., *Genetic Engineering*, 20:143–151 (1988).

Robinson, G.S. et al., "Oligodeoxynucleotides Inhibit Retinal Neovascularization in a Murine Model of Proliferative Retinopathy," *Proc. Natl. Acad. Sci.* vol. 93:4851–4856 (1996).

Miyamoto, K. et al., "In Vivo Demonstration of Increased Leukocyte Entrapment in Retinal Microcirculation of Diabetic Rats," *Invest. Ophthalmol. Vis. Sci. 39(11)*:2190–2194 (1998).

Miyamoto K. et al., "In Vivo Quantification of Leukocyte Behavior in the Retina During Endotoxin–Induced Uveitis," *Invest. Ophthalmol. Vis. Sci. 37(13)*:2708–2715 (1996).

Nishiwaki H. et al., "Visualization and Quantitative Analysis of Leukocyte Dynamics in retinal Microcirculation of Rates," *Invest. Ophthalmol. Vis. Sci. 37(7)*:1341–1347 (1996).

Tilton, R.G. et al., "Prevention of Diabetic Vascular Dysfunction by Guanidines Inhibition of Nitric Oxide Synthase Versus Advanced Glycation End–Product Formation," *Diabetes 42(2)*:221–232 (1993).

Tilton, R.G. et al., "Vascular Dysfunction Induced by Elevated Glucose Levels in Rats is Mediated by Vascular Endothelial Growth Factor," *J. Clin. Invest.* 99(9):2192–2202 (1997).

Hynes, R.O., "Integrins: Versatility, Modulation, and Signaling in Cell Adhesion," *Cell*, 69:11–25 (Apr. 3, 1992).

Faveeuw, C., et al., "Expression of Homing and Adhesion Molecules in Infiltrated Islets of Langerhans and Salivary Glands of Nonobese Diabetic Mice," *Journal of Immunology*, 152:5969–5978(1994).

Hunger, R.E., et al., "Inhibition of Submandibular and Lacrimal Gland Infiltration in Nonobese Diabetic Mice by Transgenic Expression of Soluble TNF–receptopr p55," *J. Clin. Invest.*, 98:954–961 (1996).

Prieto, J., et al., "Induction of Intercellular Adhesion Molecule–1 (CD54) on Isolated Mouse Pancreatic β Cells by Inflammatory Cytokines," *Clinical Immunology and Immunopathology*, 65(3):247–253 (Dec., 1992).

Papaccio, G., et al., "Pancreatic duct inflammatory infiltration in the nonobese diabetic (NOD) mouse," *J. Anat.*, 185:465–470 (1994).

Guha, M., et al., "Molecular and cellular alterations in monocyte/macrophages in response to hyperglycemia and inflammatory cytokines," *Blood—Journal of the American Society of Hematology*, 90(10): Abstract No. 2882 (Nov. 15, 1997).

Yoshioka, N., et al., "PS 49 Retinopathy—Experimental and Pathogenesis," *Diabetologia—Journal of the European Association for the Study of Diabetes*, 40(1): Abstract No. 1925 (Jun. 1997).

DeSouza, C.A., et al., "Elevated levels of Circulating Cell Adhesion Molecules in Uncomplicated Essential Hypertension," *The FASEB Journal*, 11(3):Abstract No. 2696 (Feb. 28, 1997).

Vejlsgaard, G.L., et al., "Kinetics and characterization of intercellular adhesion molecule–1 (ICAM–1) expression on keratinocytes in various inflammatory skin lesions and malignant cutaneous lymphomas," *J. Am. Acad. Dermatol.*, 20:782–790 (1989).

Luscinskas, F.W., et al., "Integrins and dynamic regulators of vascular function", *FASEB J.*, 8:929–938 (1994).

Rosales, C., et al., "Signal transduction by cell adhesion receptors in leukocytes", *Leukocyte Biol*, 57:189–198 (1995).

Braun, R.D., et al., "Decreased deformability of Polymorphonuclear leukocytes in diabetic cats", *Microcirculation*, 3:271–278 (1996).

Miyamoto, K., et al., "Prevention of leukostasis and vascular leakage in streptozotocin–induced diabetic retinopathy via intercellular adhesion molecule–1 inhibition", *Proc Natl Acad Sci USA*, 96(19):10836–10841 (1999).

Diamond, D.S., et al., "A subpopulation of Mac–1 (CD11b/CD18) molecules mediates neutrophil adhesion to ICAM–1 and fibrinogen", *J Cell Biol*, 120:545–556 (1993).

Davenpeck, K.L., et al., "Rat neutrophils express alpha4 and beta1 integrins and bind to vascular cell adhesion molecule–1 (VCAM–1) and mucosal addressin cell adhesion molecule–1 (MadCAM–1)", *Blood*, 91:2341–2346 (1998).

Morohoshi, M., et al., "Glucose–dependent interleukin 6 and tumor necrosis factor production by human peripheral blood monocytes in vitro", *Diabetes*, 45:954–959 (1996).

Kim, J.A., et al., "Evidence that glucose increases monocyte binding to human aortic endothelial cells", *Diabetes*, 43:1103–1107 (1994).

Manduteanu, I., et al., "High glucose induces enhanced moncyte adhesion to valvular endothelial cells via a mechanism involving ICAM–1, VCAM–1 and CD18", *Endothelium*, 6:315–324 (1999).

Springer, T.A., "Adhesion receptors of the immune system," *Nature (London)*, 346:425–434 (1990).

Luscinskas, F.W., et al., "Cytokine–Activated Human Endothelial Monolayers Support Enhanced Neutrophil Transmigration via a Mechanism Involving Both Endothelial–Leukocyte Adhesion Molecule–1 and Intercellular Adhesion Molecule–1," *J. Immunol.*, 146:1617–1625 (1991).

Del Maschio, A., et al., "Polymorphonuclear Leukocyte Adhesion Triggers the Disorgainzation of Endothelial Cell-to–Cell Adherens Junction," *J. Cell Biol.*, 135:497–510 (1996).

Bolton, S.J., et al., "Loss of the Tight Junction Proteins Occludin and Zonula Occludens–1 from Cerebral Vascular Endothelium During Neutrophil–Induced Blood–Brain Barrier Breakdown In Vivo," *Neuroscience*, 86:1245–1257 (1998).

Kurose, I., et al., "Molecular Determinants of Reperfusion–Induced Leukocyte Adhesion and Vascular Protein Leakage," *Circ. Res.*, 74:336–343 (1994).

Vinores, S.A., et al., "Rapid Communication," *Am. J. Pathol.*, 134:231–235 (1989).

Yamana, Y., et al., "Reflow of obstructed capillaries in the maculae of humans with diabetic retinopathy, observed by fluorescein angiography," *Br. J. Ophthalmol.*, 72:660–665 (1988).

Bandello, F., et al., "Spontaneous Regression of Neovascularization at the Disk and Elsewhere in Diabetic Retinopathy," *Am. J. Ophthalmol.*, 122:494–501 (1996).

Takahaashi, K., et al., "Reperfusion of Occluded Capillary Beds in Diabetic Retinopathy," *Am. J. Ophthalmol.*, 126:791–797 (1998).

Wierusz–Wysocka, B., et al., "Evidence of Polymorphonuclear Neutrophils (PMN) Activation in Patients with Insulin–Dependent Diabetes Mellitus," *J. Leukocyte Biol.*, 42:519–523 (1987).

Lutty, G.A., et al., "Relationship of Polymorphonuclear Leukocytes to Capillary Dropout in the Human Diabetic Choroid," *Am. J. Pathol.*, 151:707–714 (1997).

Tolentino, M.J., et al., "Intravitreal injections of vascular endothelial growth factor produce retinal ischemia and microangiopathy in an adult primate", *Ophthalmology*, 103:1820–1828 (1996).

Okamoto, N., et al., "Transgenic mice with increased expression of vascular endothelial growth factor in the retina", *Am. J. Pathol.*, 151:281–291 (1997).

Aiello, L.P., et al., "Vascular endothelial growth factor–induced retinal permeability is mediated by protein kinase C in vivo and suppressed by an orally effective beta–isoform-selective inhibitor", *Daibetes*, 46:1473–1480 (1997).

Adamis, A.P., et al., "Increased vascular endothelial growth factor levels in the vitreous of eyes with proliferative diabetic retinopathy", *Am. J. Ophthalmol.*, 118:445–450 (1994).

Aiello, L.P., et al., "Vascular endothelial growth factor in ocular fluid of patients with diabetic retinopathy and other retinal disorders", *N Eng J Med*, 331:1480–1487 (1994).

Malecaze, F., et al., "Detection of vascular endothelial growth factor messanger RNA and vascular endothelial growth factor–like activity in proliferative diabetic retinopathy", *Arch. Ophthalmol.*, 112:1476–1482 (1994).

Melder, R.J., et al., "During angiogenesis, vascular endothelial growth factor and basic fibroblast growth factor regulate natural killer cell adhesion to tumor endothelium", *Nature Med*, 2:992–997 (1996).

Becker, M.D., et al., "In vivo significance of ICAM–1–dependent leukocyte adhesion in early corneal angiogenesis", *Invest. Ophthalmol. Vis. Sci.*, 40:612–618 (1999).

Detmar, M., et al., "Increased microvascular density and enhanced leukocyte rolling and adhesion in the skin of VEGF transgenic mice", *J Invest Dermatol*, 111:1–6 (1998).

Yaccino, J.A., et al., "Physiological transport properties of cultured retinal microvascular endothelial cell monolayers", *Curr Eye Res*, 16:761–768 (1997).

Esser, S., et al., "Vascular endothelial growth factor induces endothelial fenestrations in vitro", *J Cell Biol*, 140:947–959 (1998).

Roberts, W.G., et al., "Increased microvascular permeability and endothelial fenestration induced by vascular endothelial growth factor", *J Cell Sci*, 108:2369–2379 (1995).

Roberts, W.G., et al., "Neovasculature induced by vascular endothelial growth factor is fenestrated", *Cancer Res*, 57:765–772 (1997).

Shen, H., et al., "Characterization of vascular permeability factor/vascular endothelial growth factor receptors on mononuclear phagocytes", *Blood*, 81:2767–2773 (1993).

* cited by examiner

FIG. 11A
FIG. 11B
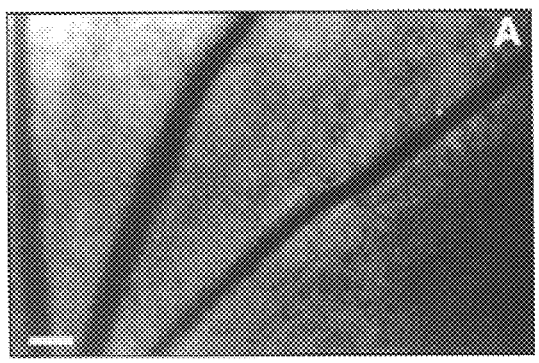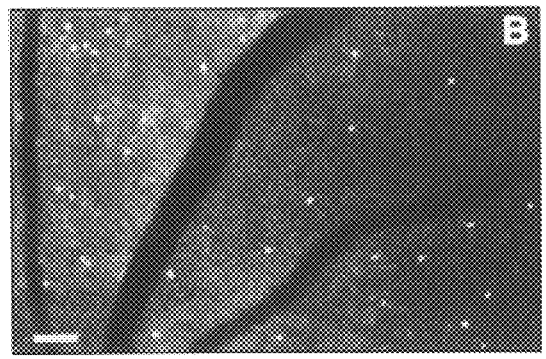

FIG. 15A
FIG. 15B
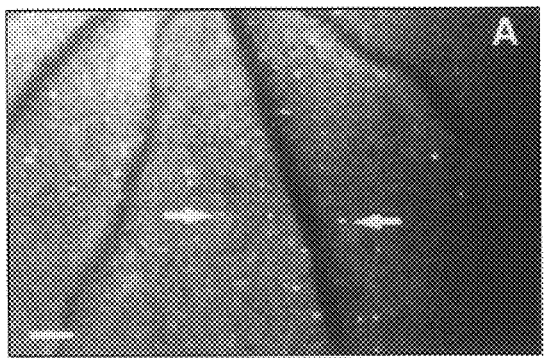

PREVENTION AND TREATMENT OF RETINAL ISCHEMIA AND EDEMA

RELATED APPLICATION

This application is a Continuation-in-Part of U.S. application Ser. No. 09/248,752, filed Feb. 12, 1999, entitled, "The Prevention and Treatment for Retinal Ischemia and Edema," and claims the benefit of U.S. Provisional Application No. 60/114,221, filed Dec. 30, 1998, entitled, "The Prevention and Treatment for Retinal Ischemia and Edema," the entire teachings of which are incorporated herein by reference.

GOVERNMENT SUPPORT

The invention was supported, in whole or in part, by a grant 2P01 HL32262-15 from the National Institutes of Health. The Government has certain rights in the invention.

BACKGROUND OF THE INVENTION

Diabetes affects over 16 million Americans. The World Health Organization indicates that diabetes afflicts 120 million people worldwide, and estimates that this number will increase to 300 million by the year 2025. Diabetics are faced with numerous complications including kidney failure, non-traumatic amputations, an increase in the incidence of heart attack or stroke, nerve damage, and loss of vision. Diabetic retinopathy is a form of visual impairment suffered by diabetics.

In particular, diabetic retinopathy is responsible for 13.1% and 18.2% newly reported cases of blindness for men and women, respectively. Kohner E. M., et al. *Diabetic Retinopathy Metabolism*, 25:1985–1102 (1975). The prevalence of blind diabetics in the population is about 100 people per million. Id.

Less than optimal methods of treatment for diabetic retinopathy exist. For example, laser treatment may be used to slow the progression of edema, but it cannot be used to reverse the symptoms of diabetes. Accordingly, a need exists to develop effective methods of treatment to reduce or impede vision loss and/or diabetic retinopathy.

SUMMARY OF THE INVENTION

The present invention relates to methods for inhibiting the binding of a leukocyte to an endothelial cell or another leukocyte in the retinal vasculature. The present invention pertains to methods of treating (e.g., reducing or preventing) retinal injury in a mammal (e.g., human, individual, patient) wherein the injury involves retinal edema or retinal ischemia, comprising administering a compound that inhibits the binding of a leukocyte to endothelium or to another leukocyte wherein a reduction in edema or ischemia (e.g., non-perfusion) occurs. The compound comprises an integrin antagonist (e.g., lymphocyte function associated molecule-1 (LFA-1), Mac-1 or p150,95), a selectin (e.g., P-selectin, E-selectin and L-selectin) antagonist, an adhesion molecule antagonist (e.g., Intercellular Adhesion Molecule (ICAM)-1, ICAM-2, ICAM-3, Platelet Endothelial Adhesion Molecule (PCAM), Vascular Cell Adhesion Molecule (VCAM)), or a leukocyte adhesion-inducing cytokine or growth factor antagonist (e.g., Tumor Necrosis Factor-α (TNF-α), Interleukin-1 β(IL-1 β), Monocyte Chemotatic Protein-1 (MCP-1) and a Vascular Endothelial Growth Factor (VEGF)). The integrin antagonist can be an integrin subunit (e.g., CD18 or a CD11b) antagonist. The antagonist can be administered with or without a carrier (e.g., pharmaceutically acceptable carrier).

In particular, the invention pertains to methods of treating or preventing retinal injury in a mammal comprising administering to the mammal an adhesion molecule antagonist and/or an integrin antagonist, wherein the adhesion molecule antagonist and/or the integrin antagonist inhibits leukocyte interaction, thereby reducing or preventing retinal injury. The antagonist can be administered in a carrier (e.g., a pharmaceutically acceptable carrier). The antagonist for adhesion molecule can be a VCAM, PCAM, ICAM-2 or ICAM-3 antagonist or, preferably, an ICAM-1 antagonist. In particular, the antagonist can be an antibody or an antibody fragment which is specific for ICAM-1, an antisense molecule that hybridizes to the nucleic acid sequence which encodes ICAM-1, or a peptide mimetics molecule, a ribozyme, an aptamer, or a small molecule antagonist that inhibits ICAM-1. The integrin antagonist can be a LFA-1 antagonist, Mac-1 antagonist or p150,95 antagonist. The integrin antagonist also comprises an integrin subunit antagonist (e.g.,a CD18 antagonist and/or a CD11b antagonist). The antagonist can be an antibody or antibody fragment specific for CD18 and/or CD11b, an antisense molecule that hybridizes to the nucleic acid sequence that encodes CD18 and/or CD11b, or a peptide mimetic molecule, a ribozyme, an aptamer or a small molecule antagonist that inhibits CD18 or CD11b.

Another aspect of the invention includes a method for preventing or treating an individual having retinal injury (e.g., injury caused by diabetic retinopathy), wherein the injury is associated with retinal edema and/or retinal ischemia, comprising administering to the individual a compound that inhibits Mac-1 or a pathway thereof. The compound inhibits ICAM-1, CD18, CD11b, and/or VEGF, and causes a decrease of ischemia and/or edema (e.g., between about 10% and about 90%). Leukocyte interaction can also be reduced. The compound can be an antibody, an antibody fragment, a peptide mimetic molecule, an antisense molecule, a ribozyme, an aptamer and/or a small molecule antagonist. Examples for such a compound are ICAM-1, CD18, CD11b, and/or VEGF.

The invention also pertains to a method of treating an individual having retinopathy or at risk for retinopathy (e.g., diabetic retinopathy) comprising administering an antagonist (e.g., ICAM-1, CD18, CD11b and/or VEGF), as described herein. The antagonist can optionally be administered in a suitable carrier (e.g., pharmaceutically acceptable carrier). Administration of this antagonist results in a decrease in retinal ischemia and/or retinal edema. Preferably, a decrease in ischemia and/or edema occurs by at least about 10%, and more preferably, by about 20%, 30%, 40%, 50%, 60%, 70%, 80%, 90%, 95% (e.g., between 10% and 95%). Accordingly, the present invention also relates to methods for treating or preventing retinal edema and/or retinal ischemia comprising administering an ICAM antagonist (e.g., ICAM-1), a CD18 antagonist, a CD11b antagonist and/or a VEGF antagonist, wherein a decrease in the edema and/or ischemia occurs.

The present invention also relates to methods of treating diabetic retinopathy by administering an ICAM-1, CD18, CD11b and/or VEGF antagonist and at least one additional antagonist that inhibits the binding of a leukocyte to an endothelial cell or to another leukocyte. The additional antagonist can be an integrin antagonist (e.g., an integrin subunit antagonist such as CD18 and/or CD11b), a selectin antagonist, a leukocyte adhesion-inducing or growth factor antagonist, or adhesion molecule antagonist. The additional antagonist can be, for example, another ICAM antagonist (e.g., an antagonist that is specific for a different portion or epitope of the ICAM-1 molecule), a PCAM antagonist or a VCAM antagonist. The types of integrin antagonists, selectin antagonists, and leukocyte adhesion-inducing or growth factor antagonists are described herein.

The invention also encompasses a method of inhibiting leukocyte interaction, comprising contacting a leukocyte, an endothelial cell or a leukocyte adhesion-inducing cytokine, with a compound or antagonist, as defined herein. The compound can be an integrin antagonist (e.g., an integrin sub-unit antagonist such as CD18 and/or CD11b), a selectin antagonist, an adhesion molecule antagonist or a leukocyte adhesion-inducing cytokine or growth factor antagonist. In particular, the invention relates to a method of inhibiting leukocyte interaction, comprising contacting an endothelial cell with an adhesion molecule antagonist (e.g., ICAM-1 specific antagonist), an integrin subunit antagonist (e.g., CD18 and/or CD11b specific antagonist), or a leukocyte adhesion-inducing cytokine antagonist or growth factor antagonist (e.g., TNF-1α, IL-1β, MCP-1 and VEGF antagonist).

The invention also pertains to a method of preventing or reducing retinal leukostasis an a mammal comprising administering to the mammal an effective amount of an ICAM, CD18, CD11b and/or VEGF antagonist. The types of antagonist is described herein. The method results in retinal leukostasis reduction by between about 10% and 90o%.

Another aspect of the invention is a method of decreasing retinal leukocyte adhesion in a mammal, comprising administering to the mammal an effective amount of an antagonist that is specific for CD11b, CD18 or a combination thereof. The retinal leukocyte adhesion is decreased between about 10% and 90%.

Yet another aspect of the invention is a method of treating or preventing neovascularization in a mammal, comprising administering to the mammal a CD18 antagonist and an ICAM-1 antagonist, or a CD18 antagonist. The types of antagonists are described herein. The method is applicable to diseases or conditions associated with neovascularization including, but not limited to, age-related macular degeneration, choroidal neovascularization, sickle cell retinopathy, retina vein occlusion, diabetic retinopathy, a condition associated with limbal injury, a condition associated with increased neovascularization, traumatic alkali injury, Stevens Johnson syndrome and ocular cicatricial pemphagoid. The neovascularization can be reduced in the cornea, the retina or the choroid.

Advantages of the present invention include effective treatment for retinopathy, retinal edema, retinal ischemia, neovascularization and other associated disease. Treatment of these diseases and/or conditions have been ineffective until the discovery of the present invention. For the first time, the present invention provides useful methods of treatment which target molecules that are involved in these diseases.

BRIEF DESCRIPTION OF THE FIGURES

FIG. 2A and FIG. 2B show the retinal area after seven days of diabetes. FIG. 2C and FIG. 2D show the retinal area after eight days of diabetes. FIGS. 2A and FIGS. 2C are photographs from orange leukocyte fluorography (AOLF) and FIGS. 2B and FIGS. 2D are photographs from fluorescein angiography. Scale bar denotes 100 μm (3.2 pixel=1 μm).

FIGS. 3A and 3B show the retinal area after one week, FIGS. 3C and 3D show the retinal area after two weeks, and FIGS. 3E and 3F show the retinal area after four weeks. FIGS. 3A, 3C, and 3E are photographs from AOLF and FIGS. 3B, 3D and 3F are photographs from fluorescein angiography. Scale bar denotes 100 μm (3.2 pixel=1 μm).

FIGS. 11A–B are photographs of AOLF retina before (FIG. 11A) and 48 hours after a 50 ng Vascular Endothelial Growth Factor (VEGF) injection (FIG. 11B). Scale bar denotes 100 µm (3.2 pixel=1 µm).

FIGS. 15A–B are photographs of retina 48 hours after rats were injected intravitreously with 50 ng (FIG. 15A) followed by fluorescein angiography (FIG. 15B). Arrows indicate areas of capillary non-perfusion downstream from static leukocytes. Scale bar denotes 100 µm (3.2 pixel=1 µm).

FIG. 16A is a photograph showing results of a ribonuclease protection that demonstrated that retinal ICAM-1 levels were significantly increased 20 h following the intravitreous delivery of 50 ng VEGF. Control animals received 5 µl of PBS solvent alone. Each lane shows the signal from one retina of one animal. The lane labeled "Probes" shows a hundred-fold dilution of the full-length ICAM-1 and 18S riboprobes. The lanes labeled "RNase–(0.1)" and "RNase–(0.01)" show the ten-fold and hundred-fold dilutions, respectively, of the full-length riboprobes without sample or RNase. The lane labeled "RNase 30" shows the full-length riboprobes with RNase, but without sample. FIG. 16B is a bar graph showing the amount of normalized ICAM-1 mRNA in the retina (arbitrary units, mean+SD) for rats injected with the vehicle alone and with 50 ng of VEGF. NS=not significant.

FIG. 17A is a bar graph showing the retinal vascular [$^{125}$I]albumin permeation (µg plasma×g tissue wet weight$^{-1}$×min$^{-1}$, mean+SD) for rats that were untreated, or treated with the vehicle alone, 50 ng VEGF, 50 VEGF and mouse IgG1, or 50ng VEGF and an anti-ICAM-1 antibody. FIG. 17B is a bar graph showing the density of trapped leukocytes ($\times 10^{-5}$ cells/pixel$^2$, mean=SD) in the retina using AOLF for untreated rats or rats treated with treated with the vehicle alone, 50 ng VEGF, 50 VEGF and mouse IgG1, or 50 ng VEGF and an anti-ICAM-1 antibody. ICAM-1 bioactivity was inhibited via intravenous administration of ICAM-1 neutralizing antibody and retinal permeability (FIG. 17A) or leukostasis (FIG. 17B) were evaluated, respectively. NS=not significant.

DETAILED DESCRIPTION OF THE INVENTION

Figure 1A:
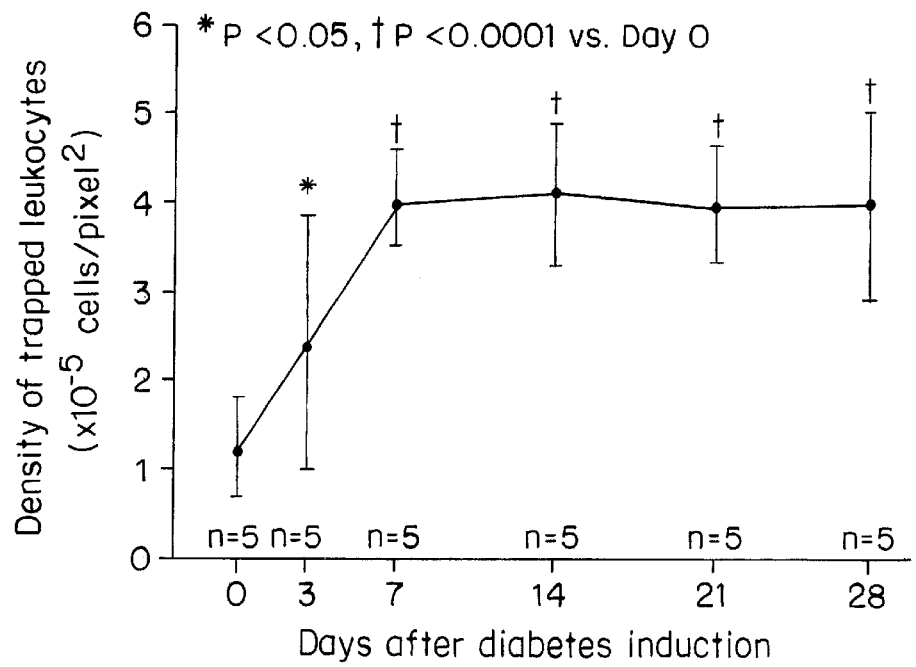
FIG. 1A is a graph showing the density of trapped leukocytes as measured on 0, 3, 7, 14, 21 and 28 days after diabetes induction. The graph shows a time course of diabetic retinal leukostasis. All data show the mean±the standard deviation (SD).

The invention relates to methods of treating and/or preventing retinal injury in a mammal by administering to the mammal a compound that inhibits leukocyte interaction which is the binding of a leukocyte to an endothelial cell or to another leukocyte. Several antagonists inhibit leukocyte interaction and include an integrin antagonist, a selectin antagonist, an adhesion molecule antagonist, or a leukocyte adhesion-inducing cytokine antagonist or growth factor antagonist. In particular, an intercellular adhesion molecule-1 antagonist, a CD18 antagonist, a CD11b antagonist or a VEGF antagonist are encompassed by the present method. Administration of such antagonists results in a significant decrease in retinal edema and/or retinal ischemia. The retinal injury can be caused by retinopathy or a visually-related disease that involves leukocyte occlusion in blood vessels (e.g., capillaries) and their destruction (e.g., atrophy). In particular, the present methods pertain to treating diabetic retinopathy.

Diabetic retinopathy is a progressive degeneration of retinal blood vessels and is a consequence of diabetes, in particular, diabetes mellitus. One important aspect of the disease is retinal edema. Fluid build up from deteriorating blood vessels and capillaries causes edema. As the disease progresses, the damage proliferates and large hemorrhages and retinal detachment can result.

The term "retinopathy" also refers to noninflammatory degenerative diseases of the retina. The methods of the present invention encompass retinopathy or a visually-related disease that is characterized by one or more of the following retinal signs: capillary obstruction, nonperfusion, leukostasis, formation of vascular lesions and/or proliferation of new blood vessels in association with ischemic areas of the retina. Leukostasis refers to the stasis or non-movement of white blood cells (e.g., leukocytes) in the vasculature. Other disorders or diseases implicated by the invention involve diseases which result in retinal edema and/or retinal ischemia. Examples of such diseases include vein occlusions, sickle cell retinopathy, radiation retinopathy, diabetic retinopathy, VEGF-induced diseases and retinopathy prematurity.

Capillary occlusions constitute a characteristic pathologic feature in diabetic retinopathy, and, when widespread, initiate neovascularization. Neovascularization (e.g., angiogenesis) refers to the formation or growth of new blood vessels. Microaneurysms, intraretinal microvascular abnormalities and vasodilation also are commonly found in early stages of diabetic retinopathy and have been correlated to capillary occlusions. Schroder, S. et al., *American Journal of Pathology*, 139 (81), 81–100 (1991). Leukocytes cause capillary obstruction that is involved in diabetic retinopathy via two mechanisms. This obstruction is the result of the leukocytes' large cells volume and high cytoplasmic rigidity. Leukocytes can become trapped in capillaries under conditions of reduced perfusion pressure (e.g., caused by vasoconstriction) or in the presence of elevated adhesive stress between leukocytes and the endothelium, endothelial swelling, or narrowing of the capillary lumen by perivascular edema. Id. Examples of leukocytes include granulocytes, lymphocytes, monocytes, neutrophils, cosinophils, and basophils. Elevated adhesive stress can result from release of chemotactic factors or expression of adhesion molecules on leukocytes or endothelial cells. Secondly, leukocytes injures capillaries leading to capillary death, also known as "capillary dropout."

A number of glycoproteins are involved in the adhesion of leukocytes. In the case of neutrophils and monocytes, a family of glycoproteins, known as $\beta_2$ integrins, have been identified. This family of integrins include Lymphocyte Function Associated Antigen-1 (LFA-1), Mac-1, and p150, 95. Some integrins are made up of molecules referred to as "subunits" or "integrin subunits." The LFA-1 integrin is comprised of 2 subunits, CD11a and CD18, Mac-1 integrin is comprised of CD11b and CD18, and p150,95 is made up of CD11c and CD18.

A corresponding family of glycoproteins, referred to as selectins, are expressed in endothelial cells or can be induced by stimulation with endotoxins or cytokines. The selectins include P-selectin, E-selectin, and L-selectin. The selectin family is involved in endothelial interaction. Firm adhesion of activated polymorphonuclear neutrophils (PMN) to the endothelial cells occur through the interaction between integrins (e.g., LFA-1, MAC-1 and p150,95) expressed on the PMNs and members of the immunoglobulin superfamily of proteins, referred to as Intercellular Adhesion Molecule-1 (ICAM-1), Platelet Endothelial Adhesion Molecule (PCAM), and Vascular Cell Adhesion Molecule (VCAM), expressed by the endothelium. Additionally, cytokines such as Tumor Necrosis Factor-$\alpha$ (TNF-$\alpha$), Interleukin-1$\beta$ (IL-1 $\beta$), Monocyte Chemotatic Protein-1 (MCP-1), and growth factors (VEGF) can induce the surface expression of ICAM-1, VCAM-1, and E-selectin on endothelial cells.

Intercellular adhesion molecules are involved in and are important for inflammation responses. Mediators of inflammation cause an induction of ICAM-1 expression on various cell types and sites of inflammation. Both soluble and membrane forms of ICAM-1 exist. Roep, B. O. et al., *Lancet* 343, 1590–1593, 1590 (1994). ICAM-1 is an inducible cell surface ligand for LFA-1. Larson, R. S., et al., *Immunologzal Reviews*, 114, 181–217, 192 (1990). ICAM-1 is a single chain glycoprotein with a peptide backbone of 55 kD. ICAM-1 is a member of immunoglobulin super family consisting of 5 immunoglobulin-like domains. ICAM-1 is expressed or induced by inflammatory mediators on many cell types including endothelial cells, epithelial cells, keratinocytes, synovial cells, lymphocytes, and monocytes. The LFA-1 binding site is the first immunoglobulin domain of ICAM-1. ICAM-1 also binds with Mac-1, an important mechanism in retinal edema and retinal ischemia. Various forms of ICAM-1 can be used to generate antagonists, such as antibodies or antisense molecules.

Retinal leukostasis is a very early event in diabetic retinopathy with important functional consequences. Both retinal vascular leakage and non-perfusion follow its development. The inhibition of ICAM-1 activity blocks diabetic retinal leukostasis and potently prevents blood-retinal barrier breakdown. Leukostasis is associated with the development of vascular nonperfusion and thus its inhibition can also prevent capillary dropout. Indeed, activated leukocytes are increased in diabetes and leukocytes have been associated with capillary loss in the diabetic choroid. The data described herein demonstrate that ICAM-1-mediated leukostasis is increased in the retinal vasculature very early in diabetes and accounts for the majority of diabetes-associated retinal vascular leakage. Thus, these data, described herein, indicate ICAM-1 as a new therapeutic target for the prevention of many of the sight-threatening retinal abnormalities, especially those associated with diabetes. See Example 1.

The data described herein also show that CD11a, CD11b, and CD18 $\beta_2$ integrin levels were increased on the surface of neutrophils from diabetic rats. The increases correlated with the enhanced functional adhesiveness of diabetic neutrophils to rat endothelial cell monolayers. Similarly, in an in vivo model of experimentally-induced diabetes, use of anti-CD18 F(ab')$_2$ fragments significantly decreased diabetic retinal leukostasis by 62%, confirming the relevance of the in vitro findings. The data described herein indicate that the Mac-1 integrin complex is operative in the adhesion of diabetic neutrophils to the retinal capillary endothelium. Since a major ligand for Mac-1 is ICAM-1, these results are consistent with data, shown in Example 1, that ICAM-1 blockade prevents diabetic retinal leukostasis and blood-retinal barrier breakdown. See also Example 2.

Based on the data described herein, it is reasonable to believe that the leukocyte adhesive changes in this model of diabetes are of a systemic nature. The assayed neutrophils were isolated from the peripheral blood, and therefore reflected systemic neutrophil adhesion molecule expression and bioactivity. The causes of the surface integrin changes remain unknown, however they are likely to be linked to hyperglycemia. For example, hyperglycemia directly impacts TNF$\alpha$ expression, a cytokine known to activate integrin adhesion molecules on leukocytes. In vitro work has also shown that hyperglycemia promotes increased leukocyte adhesion to endothelium via ICAM-1 and CD18. Thus, hyperglycemia, either directly or indirectly, is a proximal stimulus for the ICAM-1 and CD18 upregulation seen in diabetes.

Also, these data show that a low-level retinal leukostasis occurs in the normal state. The same molecules that are operative in the diabetic state also mediate this presumably normal phenomenon. If the low-level leukostasis in the non-diabetic state is physiologic, then the specificity of an anti-integrin therapy can be compromised.

The results, described herein, also provide additional evidence of leukocyte involvement in the pathogenesis of diabetic retinopathy. The aggregate data indicate that diabetic retinopathy should be, in one sense, redefined as an inflammatory disease. Very early in diabetes leukocytes adhere to the vascular endothelium, trigger breakdown of the blood-retinal barrier, impede flow, and in some instances, extravasate into the retinal parenchyma. The identification of Mac-1 as a functional adhesive molecule in diabetic retinopathy provides a target for the prevention and/or treatment of the disease.

Data described herein also show that VEGF induces retinal vascular permeability and leukostasis through ICAM-1. Retinal leukostasis was also spatially linked to capillary non-perfusion. The vitreous concentration at which VEGF begins to induce these changes (12.5 nM) is within the range of vitreous VEGF concentrations observed in human eyes with diabetic retinopathy. The leukostasis observed in these studies was specific to VEGF because co-injection of a neutralizing antibody abrogated the response. Finally, these findings are consistent with our data showing VEGF-induced ICAM-1 expression in the retinal vasculature. See Example 3.

Leukocytes, via their own VEGF, serve to amplify the direct effects of VEGF when they bind to endothelium. VEGF has been demonstrated in neutrophils, monocytes, eosinophils, lymphocytes and platelets. The fact that some leukocytes possess high affinity VEGF receptors and migrate in response to VEGF makes this scenario even more likely.

The data also show that VEGF-induced capillary non-perfusion occurs downstream from areas of leukocyte adhesion. Leukocyte-mediated non-perfusion characterizes experimental diabetic retinopathy. In diabetes, patent capillaries become occluded downstream from newly arrived static leukocytes. Later, following the disappearance of the leukocytes, the capillaries reopen. Since neutrophil and monocyte diameters can exceed those of retinal capillary lumens, leukocyte-mediated flow impedance is a likely mechanism.

Taken together, these data indicate that VEGF-induced vascular permeability is mediated by ICAM-1-mediated retinal leukostasis. These data are the first to show that a non-endothelial cell type contributes to VEGF-induced vascular permeability. They are also the first to provide a mechanism for the capillary non-perfusion induced by VEGF. Given these findings, targeting ICAM-1 proves useful in the treatment of diseases characterized by VEGF-induced vascular changes, such as diabetic retinopathy.

The invention takes advantage of the surprising discovery that inhibiting integrins, and in particular the Mac-1 or a pathway thereof, results in a reduction in retinal edema and/or retinal ischemia. This reduction in both retinal edema and/or retinal ischemia provides an effective treatment for various ocular diseases, including retinopathy. In one aspect of the invention, an antagonist's biological activity refers to a compound that inhibits the Mac-1 integrin adhesion or a pathway thereof. Inhibition can occur directly (e.g., by inhibiting binding of the Mac-1 molecule or a subunit thereof such as CD18 or CD11b), or indirectly (e.g., by inhibiting a molecule that affects Mac-1 such as by inhibiting ICAM-1 expression or Vascular Endothelial Growth Factor (VEGF) expression). The surprising results of directly inhibiting Mac-1 by inhibiting Mac-1 subunits are shown in Example 2. Several molecules indirectly impact on Mac-1's biological activity (e.g., its ability to bind to ICAM-1, induce leukocyte adhesion, induce leukostasis, cause edema and/or cause ischemia). For example, ICAM-1 directly binds to Mac-1. Inhibiting ICAM-1 reduces retinal edema and ischemia. See Example 1. Similarly, VEGF mediates ICAM-1 expression in the retinal vasculature, and induces vascular permeability and non-perfusion. Inhibiting VEGF results in decreased expression of ICAM-1, and a reduction in both retinal edema and retinal ischemia. See Example 3. Additionally, TNF-$\alpha$, a cytokine, induces ICAM-1 expression, which, in turn, can stimulate and increase leukocyte adhesion. Inhibiting the TNF-$\alpha$ pathway, significantly reduces leukocyte adhesion. See Example 2. Inhibiting Mac-1 and molecules that affect the Mac-1 pathway (e.g., ICAM-1 expression) unexpectedly results in reductions of retinal edema and ischemia.

Inhibition of a molecule encompassed by the invention (e.g., Mac-1, CD18, CD11b, ICAM-1, VEGF or TNF-$\alpha$) can be accomplished in several ways. A molecule can be made inactive or its action disrupted. For example, the expression of these molecules can be inhibited prior to the molecule exiting the cell using, for example, antisense technology, etc. The molecule can also be made inactive by inhibiting its binding to a receptor after it exits the cell or is exposed on the membrane of the cell, e.g., with an antibody or antibody fragment. Additionally, the action of these molecules can be inhibited by disrupting the signaling downstream from the receptor (e.g. alterations in phosphorylation). These and other methods can be used so long as the activity or action of one or more of the molecule described herein is inhibited or disrupted.

The invention relates to preventing or treating retinal injury wherein the retinal injury involves retinal edema and/or retinal ischemia, comprising administering a compound that inhibits the binding of a leukocyte to an endothelial cell or another leukocyte in, for example, a blood vessel or capillary, which results in the reduction of retinal edema and/or retinal ischemia. The term "retinal injury" is defined herein as a decreased ability for the retina to function normally, for example, by the patient's vision, as measured, electrical signal potential, fluorescein angiograms or other known methods or methods developed in the future. The compound has the ability to inhibit or reduce leukocyte occlusion in the retinal vasculature. As described herein, the compound can be an integrin antagonist (e.g., Mac-1 antagonist), an integrin subunit antagonist (e.g., CD18 antagonist or a CD11b antagonist), a selectin antagonist, a leukocyte adhesion-inducing cytokine antagonist or growth factor antagonist (e.g., TNF-$\alpha$, IL-1$\beta$, MCP-1 and VEGF antagonist), or an adhesion molecule antagonist (e.g., an ICAM-1, ICAM-2, ICAM-3, PCAM or VCAM antagonist). In particular, the invention also pertains to administering an ICAM-1 antagonist, a VEGF antagonist, a Mac-1 antagonist, a CD18 antagonist, or a CD11b antagonist, to treat retinal edema, retinal ischemia, and/or diabetic retinopathy. The various forms of the antagonists are described herein.

The methods described herein can be used for treating ocular tissue that experiences leukostasis, edema and/or ischemia. Such tissue includes the retina, and the choroid. For example, the invention includes a method of treating or reducing leukostasis, edema and/or ischemia in the retina or the choroid of an affected mammal by administering to the mammal one or a combination of any one of the antagonists described herein.

The invention includes methods of inhibiting leukocyte interaction, comprising contacting a leukocyte or endothelial cell with an antagonist. For example, using the various antagonists described herein, one can contact a leukocyte with an integrin antagonist, an endothelial cell with an adhesion molecule antagonist or a selectin antagonist, or subject the cytokines that induce surface expression of ICAM-1, VCAM-1, and E-selectin to a leukocyte adhesion-inducing cytokine antagonist.

The invention further comprises the use of an ICAM-1, a CD18, a CD11b or a VEGF antagonist in conjunction with a second antagonist. Genetic variability that exists among various patient populations and/or additional mechanisms can warrant administering more than one antagonist. Any combination of the above antagonists can be used. For example, the present methods include administering an ICAM-1 antagonist, which is specific to a particular epitope of ICAM-1, and an additional ICAM-1 antagonist, which is specific to a different epitope or genetic variation. Similarly, an ICAM-1 antagonist can be administered with any one of the antagonists described herein. Administering a combination of antagonists to prevent the leukocyte adhesion to endothelial cells and/or leukocytes results in even more effective treatment of diabetic retinopathy or a more dramatic reduction in retinal edema and/or ischemia. See Example 2 in which both a CD18 and CD11b antagonist was used to reduce leukocyte adhesion. Given the causal effect of leukocyte adhesion on retinal edema and/or ischemia, as proven by the data, administration of a CD18 and/or CD11b antagonist is expected to reduce retinal edema and/or retinal ischemia. The combination of antagonists can be administered at substantially the same time, or sequentially, with suitable intervals between administration of the antagonists to confer the desired effect.

The invention also relates to decreasing or reducing the amount of ischemia and/or edema present in an individual by administering an effective amount of an ICAM-1 a CD18, a CD11b or a VEGF antagonist. Ischemia refers to tissue which lacks proper or suitable blood flow. Ischemia refers to an inadequate circulation of blood flow which can be the result of a mechanical obstruction (e.g., trapped leukocyte) of the blood supply or damage to the blood supplying vessel which results in a reduction of the blood flow. Inadequate blood flow results in reduced tissue oxygenation. Hence, ischemia can be a function of leukostasis, and can be measured by determining the density of trapped leukocytes, and other methods known in the art or developed in the future as described herein.

Edema refers to the build up of excess fluid caused by vasculature leakage (e.g., vascular permeability). Edema also refers to the build up or accumulation of fluid when the fluid is not timely or properly cleared. As described herein, leukocytes become trapped in the capillaries in the conditions of reduced perfusion pressure (e.g., caused by constriction as seen in early stages of diabetes) or in the presence of an elevated adhesive stress between leukocytes and endothelium, endothelial swelling or narrowing of the capillary lumen by perivascular edema. The leukocyte build up can cause leakage from the blood vessel. Thus, edema can be measured by determining the amount of retinal vascular albumin permeation, as referred to as "vascular permeability," as described herein.

The methods of treatment described herein include reducing or decreasing the amount of ischemia and/or edema by administering antagonist that inhibits leukocyte and endothelial cell interaction, as described herein. The decrease in ischemia is at least about 10% and can be greater, such as at least about 20%, 30%, 40%, 50% 60%, 70%, 80%, 90%, or 95%. The decrease in edema is at least about 10%, and can be greater, such as at least about 20%, 30%, 40%, 60%, 70%, 80%, 90%, and preferably at least about 95%.

The reduction or decrease of the retinal edema and/or retinal ischemia can be determined, as compared to a control, standard, or baseline. For example, a measure of edema or ischemia can be made, in a mammal, prior to administering one of the compounds described herein, and one or more times subsequent to administration. A percentage change between two or more measurements, or a value reflecting the change in the measurements can be determined. The level of edema and/or ischemia can be quantified using methods known in the art, and a decrease, as compared with a control, standard, or baseline, indicates successful treatment. The quantified amounts of edema and/or ischemia can be compared with a suitable control to determine if the levels are decreased. The sample to be tested can be compared with levels for the specific individual from previous time points (e.g., before having diabetic retinopathy, or during various phases of treatment for the diabetic retinopathy), or with levels in normal individuals (e.g., an individual without the disease) or suitable controls. An individual who is being treated for diabetic retinopathy can be monitored by determining the levels of edema and/or ischemia at various time points. Such levels of edema and/or ischemia can be determined before treatment, during treatment, and after treatment. A decrease in the level of ischemia and/or edema, as described herein, indicates successful treatment. Ischemia and/or edema can be measured using methods now known or those developed in the future. See Kohner E. M., et al. *Diabetic Retinopathy Metabolism*, 25:1985–1102 (1975). For example, ischemia and edema can be measured using a fluorescein angiogram or by measuring the vision loss in a patient. Edema can also be assessed by measuring electrical signals or potential, visualizing the retina using a slit lamp, fluorescein angiogram, or by using a sensitive isotope dilution method.

Another aspect of the invention includes method for treating or preventing neovascularization. One of the more difficult problems in ophthalmology is treating the ocular surface abnormalities that accompany limbal cell injury. The limbus is a specialized tissue that marks the transition between cornea and conjunctiva. Stem cells reside in this area and give rise to the normal corneal epithelium. When the limbus is sufficiently destroyed, an inflammatory corneal neovascularization ensues and a conjunctiva-like epithelium covers the cornea. The latter lacks the smoothness and cohesion of the normal corneal epithelium, making it optically inferior and prone to erosions. Corneal neovascularization, and the serum it delivers via leaky vessels, supports the abnormal conjunctiva-like surface that covers the cornea. The selective injury of corneal vessels produced a reversion to a more normal corneal epithelial phenotype. Huang, A. et al., *Ophthal*. 95:228 (1988). Unlike the experimental model, the laser injury of corneal vessels has not seen long-term success in humans. Thus, an effective treatment for the corneal neovascularization that follows limbal injury has previously remained an elusive goal.

Corneal neovascularization secondary to limbal injury requires, in part, vascular endothelial growth factor (VEGF). VEGF induces intercellular adhesion molecule-1 (ICAM-1) expression in the vasculature of various tissues. Further, exogenous VEGF induces the adhesion of leukocytes to the endothelium of ocular surface vessels, a process that can be partially blocked with anti-ICAM-1 antibodies. The effect of ICAM-1 and its common ligand the $\beta_2$ integrin CD18 was tested, on limbal injury-associated corneal neovascularization and inflammation in a pathophysiologically-relevant model.

Corneal neovascularization leads to vision loss in eyes that have undergone extensive injury to the limbus. This situation characterizes a number of conditions, including traumatic alkali injury, Stevens Johnson syndrome and ocular cicatricial pemphagoid. Other conditions that involve neovascularization are diseases such as age-related macular degeneration, choroidal neovascularization, sickle cell retinopathy, retina vein occlusion, diabetic retinopathy, a condition associated with limbal injury and a condition associated with increased neovascularization. To date, no treatments have proven effective at preventing the neovascularization associated with these conditions. A pathophysiologically-relevant mouse model of limbal injury was utilized to test the role of CD18 and intercellular adhesion molecule-1 (ICAM-1) in the production of corneal neovascularization. The data described herein show that CD18 and ICAM-1 deficient mice have 39% (n=5, p=0.0054) and 33% (n=5, p=0.013) less neovascularization, respectively, when compared to strain-specific normal controls. Corneal neutrophil counts were reduced by 66% (n=5, p=0.0019) and 39% (n=5, p=0.0016) in the CD18 and ICAM-1 deficient mice, respectively. Taken together, these data identify CD-18 and ICAM-1 as important mediators of the inflammation-associated neovascularization that follows limbal injury. CD18 and ICAM-1 also serve as therapeutic targets for the treatment of the corneal neovascularization associated with limbal injury.

Hence, another embodiment of the invention includes methods of treating or preventing ocular (e.g., corneal, retinal or choroid) neovascularization in a mammal (e.g., an individual) by administering to the mammal a CD18 antagonist and an ICAM-1 antagonist or CD18 antagonist. The inhibition of both CD18 and ICAM-1, or CD18, result in significantly less neovascularization, or as compared to a control, as defined herein. See Example 4.

Hence, the present methods utilize various forms of antagonists. An antagonist, as defined herein, means a compound that can inhibit, either partially or fully, the binding of a leukocyte to an endothelial cell or to another leukocyte. An antagonist's biological activity also refers to a compound that can reduce or lessen the interaction between a leukocyte and an endothelial cell, or another leukocyte.

The terms, "antagonist" or "antibody," include proteins and polypeptides that are integrin (e.g., LFA-1, Mac-1 or p150,95) antagonists, integrin subunit (CD18, CD11a or CD11b) antagonists, adhesion molecule (e.g., ICAM, PCAM or VCAM) antagonists, selectin(e.g., P-selectin, L-selectin or E-selectin) antagonists, or leukocyte adhesion-inducing cytokine antagonists or growth factor antagonists (e.g. antagonists to TNF-α, IL-1β, MCP-1 or VEGF). These terms also include proteins and polypeptides that have amino acid sequences analogous to the amino acid sequence of the protein, as described herein, and/or functional equivalents thereof. These terms also encompass various analogues, homologues, or derivatives thereof. Analogous amino acid sequences are defined to mean amino acid sequences with sufficient identity to the antagonist's amino acid sequence so as to possess its biological activity. For example, an analogous peptide can be produced with "silent" changes in amino acid sequence wherein one, or more, amino acid residues differ from the amino acid residues of the protein, yet still possess its biological activity. Examples of such differences include additions, deletions, or substitutions of residues of the amino acid sequence of the protein or polypeptide. Also encompassed by these terms, are analogous polypeptides that exhibit greater, or lesser, bioloeal activity of the antagonist.

Antagonists also include antibody or antibody fragments, peptide mimetics molecules, antisense molecules, ribozymes, aptamers (nucleic acid molecules), and small molecule antagonists. Soluble forms of molecules (e.g., soluble ICAM) can also act as an antagonist because it can bind to the leukocyte, thereby preventing the membrane bound form from binding.

The term "antagonist" and "nucleic acid sequence" include homologues, as defined herein. The homologous proteins and nucleic acid sequences can be determined using methods known to those of skill in the art. Initial homology searches can be performed at NCBI against the GenBank (release 87.0), EMBL (release 39.0), and SwissProt (release 30.0) databases using the BLAST network service. Altshul, S F, et al, *J. Mol. Biol.* 215: 403 (1990); Altschul, S F., *Nucleic Acids Res*. 25:3389–3402 (1998), the teachings of both are incorporated herein by reference. Computer analysis of nucleotide sequences can be performed using the MOTIFS and the FindPatterns subroutines of the Genetics Computing Group (GCG, version 8.0) software. Protein and/or nucleotide comparisons can also be performed according to Higgins and Sharp (Higgins, D. G. and P. M. Sharp, "Description of the method used in CLUSTAL," *Gene*, 73:237–244 (1988)). Homologous proteins and/or nucleic acid sequences are defined as those molecules with greater than 70% sequences identity and/or similarity (e.g., 75%, 80%, 85%, 90%, or 95% homology).

Biologically active derivatives or analogs of the antagonists described herein also include peptide mimetics. Peptide mimetics can be designed and produced by techniques known to those of skill in the art. (see e.g., U.S. Pat. Nos. 4,612,132; 5,643,873 and 5,654,276, the teachings of which are incorporated herein by reference). These mimetics can be based, for example, on the protein's specific amino acid sequence and maintain the relative position in space of the corresponding amino acid sequence. These peptide mimetics possess biological activity similar to the biological activity of the corresponding peptide compound, but possess a "biological advantage" over the corresponding amino acid sequence with respect to one, or more, of the following properties: solubility, stability and susceptibility to hydrolysis and proteolysis.

Methods for preparing peptide mimetics include modifying the N-terminal amino group, the C-terminal carboxyl group, and/or changing one or more of the amino linkages in the peptide to a non-amino linkage. Two or more such modifications can be coupled in one peptide mimetic molecule. Modifications of peptides to produce peptide mimetics are described in U.S. Pat. Nos. 5,643,873 and 5,654,276, the teachings of which are incorporated herein by reference. Other forms of the proteins, polypeptides and antibodies described herein and encompassed by the present invention, include those which are "functionally equivalent." This term, as used herein, refers to any nucleic acid sequence and its encoded amino acid which mimics the biological activity of the protein, polypeptide or antibody and/or functional domains thereof.

The term, "ICAM-1 antagonist" includes antagonists that directly (e.g., by inhibiting the ICAM-1 molecules itself) or indirectly inhibit ICAM-1 (e.g., by inhibiting a molecules that affects induction of ICAM-1 such as a VEGF antagonist or a TNF-α antagonist). Such antagonist are those which lead to a reduction in edema and/or ischemia. Antagonists also include other integrin antagonists (e.g., a LFA-1 or p150,95 antagonists), selectin antagonists (e.g., P-selectin, E-selectin or L-selectin antagonist) and other adhesion molecule antagonists (e.g., ICAM-2, ICAM-3, PCAM or VCAM antagonist) or a leukocyte adhesion-inducing cytokine antagonist or growth factor antagonist (an antagonist for TNF-1α, IL-1β, MCP-1 or VEGF).

An ICAM-1 antagonist is also a composition that inhibits the binding of ICAM-1 to a receptor or has the ability to decrease or affect the function of ICAM-1. Such antagonists include antibodies to ICAM-1 (e.g., the IA29 antibody), antisense molecules that hybridize to nucleic acid which encodes ICAM-1. ICAM-1 antagonists also include ribozymes, aptimers, or small molecule inhibitors that are specific for ICAM-1 or the nucleic acid that encodes ICAM-1. Antagonists of ICAM-1 include compounds which inhibit the binding between LFA-1 or Mac-1 and ICAM-1, or compounds that reduce the biological activity or function of ICAM-1. The biological activity of ICAM-1 refers to the ability to bind to LFA-1 or, in particular, to Mac-1, the ability to induce leukocyte adhesion, the ability to cause ischemia and/or the ability to cause edema.

The terms "antibody" or "immunoglobulin" refer to an immunoglobulin or fragment thereof having specificity to a molecule involved in leukocyte-leukocyte interaction or leukocyte-endothelium interaction. Examples of such antibodies include anti-integrin antibodies (e.g., antibodies specific to LFA-1, Mac-1 or p150,35), anti-integrin subunit antibodies (e.g., antibodies specific to CD18, CD11b or a combination thereof), anti-selectin antibodies (e.g., antibodies specific to P-selection, E-selection and L-selectin), antibodies to leukocyte adhesion-inducing cytokine antagonists or growth factor antagonists (e.g., TNF-α, IL-1β, MCP-1 and VEGF antibodies), and adhesion molecule antibodies (e.g., ICAM-1, ICAM-2, ICAM-3, PCAM or VCAM antibodies). For example, the terms "ICAM-1 antibody," or "ICAM-1 immunoglobulin" refer to immunoglobulin or fragment thereof having specificity for ICAM-1.

The term, "antibody" is also intended to encompass both polyclonal and monoclonal antibodies including transgenically produced antibodies. The terms polyclonal and monoclonal refer to the degree of homogeneity or an antibody preparation and are not intended to be limited to particular methods of production. An antibody can be raised against an appropriate immunogen, such as an isolated and/or recombinant polypeptide (e.g., ICAM-1, CD18, CD11b, VEGF, or TNF-α) or portion thereof (including synthetic molecules such as synthetic peptides). In one embodiment, antibodies can be raised against an isolated and/or recombinant antigen or portion thereof (e.g., a peptide) or against a host cell which expresses recombinant antigen or a portion thereof. In addition, cells expressing recombinant antigen (e.g., ICAM-1, CD18, CD11b, VEGF, or TNF-α), such as transfected cells, can be used as immunogens or in a screening for an antibody which binds the receptor.

Preparation of immunizing antigen, and polyclonal and monoclonal antibody production, can be performed using any suitable technique. A variety of methods have been described (see e.g., Kohler et al., *Nature*, 256:495–497 (1975) and *Eur. J Immunol.* 6: 511–519 (1976); Milstein et al., *Nature* 266:550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)).

Following immunization, anti-peptide antisera can be obtained from the immunized animal, and if desired, polyclonal antibodies can be isolated from the serum. As described herein, purified recombinant proteins generated in *E. coli* were used to immunize rabbits to generate specific antibodies directed against the antigen. These antibodies recognize the recombinant protein expressed in *E. coli*. Monoclonal antibodies can also be produced by standard techniques which are well known in the art (Kohler and Milstein, *Nature* 256:495–497 (1975); Kozbar et al., *Immunology Today* 4:72 (1983); and Cole et al., Monoclonal Antibodies and Cancer Therapy, Alan R. Liss, Inc., pp. 77–96 (1985)). Generally, a hybridoma is produced by fusing a suitable immortal cell line (e.g., a myeloma cell line such as SP2/0) with antibody producing cells. The antibody producing cell, preferably those of the spleen or lymph nodes, can be obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity can be used, including, for example, methods which select recombinant antibody from a library, by PCR, or which rely upon immunization of transgenic animals (e.g., mice) capable of producing a full repertoire of human antibodies (see e.g., Jakobovits et al., *Proc. Natl. Acad. Sci. USA*, 90:2551–2555 (1993); Jakobovits et al., *Nature*, 362:255–258 (1993); Lonberg et al., U.S. Pat. No. 5,545,806; Surani et al., U.S. Pat. No. 5,545,807).

For example, the monoclonal antibody, IA29 can be used as described herein. The IA29 antibody is specific for ICAM-1, and can be purchased from R and D Systems, Minneapolis, Minnesota. Similarly, the anti-CD11a, anti-CD18, and the anti-CD11b antibodies utilized in the experiments described herein are the WT.1 mAb, 6G2 mAb and the MRC OX-42 mAb, respectively, and can be obtained from Serotec, Inc. (Raleigh, N.C.).

Functional fragments of antibodies, including fragments of chimeric, humanized, primatized, veneered or single chain antibodies, can also be produced. Functional fragments or portions of the foregoing antibodies include those which are reactive with the antigen (e.g., ICAM-1, CD18, CD11b, VEGF, or TNF-α). For example, antibody fragments capable of binding to the antigen or portion thereof, including, but not limited to, Fv, Fab, Fab' and F(ab')$_2$ fragments are encompassed by the invention. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

It will be appreciated that the antibody can be modified, for example, by incorporation of or attachment (directly or indirectly (e.g., via a linker)) of a detectable label such as a radioisotope, spin label, antigen (e.g., epitope label such as a FLAG tag) or enzyme label, flourescent or chemiluminescent group and the like, and such modified forms are included within the term "antibody."

A suitable antagonist is also an antisense molecule that can hybridize to the nucleic acid which encodes the target polypeptide (e.g., ICAM-1, CD18, CD11b, VEGF, or TNF-α). The hybridization inhibits transcription and/or synthesis of the protein. Antisense molecules can hybridize to all, or a portion of the nucleic acid. Producing such antisense molecules can be done using techniques well-known to those of skill in the art. For example, antisense molecules or constructs can be made using method known in the art. DeMesmaeker, Alain, et al., *Acc Chem. Res.* 28:366-374 (1995), Setlow, Jane K., *Genetic Engineering*, 20:143–151 (1998); Dietz, Pat. No. 5,814,500, filed Oct. 31, 1996, entitled, "Delivery Construct for Antisense Nucleic Acids and Method of Use," the teachings all of which are incorporated by reference in their entirety. In particular, constructing an antisense molecule for an ICAM-1 antagonist is described in detail in WO 97/46671, entitled, "Enhanced Efficacy of Liposomal Anti-sense Delivery," the teachings of which are incorporated by reference in their entirety. Additionally, developing an antisense molecule to inhibit a retinal disorder (e.g., retinopathy) is described in Robinson, G. S., et al., *Proc. Natl. Acad. Sci.* 93:4851–4856 (1996).

Administration and Dosages:

The terms "pharmaceutically acceptable carrier" or a "carrier" refer to any generally acceptable excipient or drug delivery device that is relatively inert and non-toxic. The antagonist can be administered with or without a carrier. A preferred embodiment is to administer the antagonist (e.g., ICAM-1 antagonist) to the retinal area or the vasculature around or leading to the retina. Exemplary carriers include calcium carbonate, sucrose, dextrose, mannose, albumin, starch, cellulose, silica gel, polyethylene glycol (PEG), dried skim milk, rice flour, magnesium stearate, and the like. Suitable formulations and additional carriers are described in Remington's Pharmaceutical Sciences, (17th Ed., Mack Pub. Co., Easton, Pa.), the teachings of which are incorporated herein by reference in their entirety. The antagonist can be administered systemically or locally (e.g., by injection or diffusion).

Suitable carriers (e.g., pharmaceutical carriers) also include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. Such preparations can be sterilized and, if desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. They can also be combined where desired with other active substances, e.g., enzyme inhibitors, to reduce metabolic degradation. A carrier (e.g., a pharmaceutically acceptable carrier) is preferred, but not necessary to administer an antagonist (e.g., an ICAM-1 antagonist).

For parenteral application, particularly suitable are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-polyoxypropylene block polymers, and the like. Ampules are convenient unit dosages.

Preferably, the antagonist is administered locally to the eye, retinal area, choroid area or associated vasculature. The antagonist can also be administered to the cornea of the eye. The antagonist diffuses into the eye and contacts the retina or surrounding vasculature (e.g., eye drops, creams or gels).

One or more antagonists described herein can be administered. When administering more than one antagonist, the administration of the antagonists can occur simultaneously or sequentially in time. The antagonists can be administered before and after one another, or at the same time. Thus, the term "co-administration" is used herein to mean that the antagonists will be administered at times to reduce leukostasis, edema and/or ischemia. The methods of the present invention are not limited to the sequence in which the various antagonists are administered, so long as the antagonists are administered close enough in time to produce the desired effect. The methods also include co-administration with other drugs that used to treat retinopathy or other diseases described herein.

The compositions of the present invention can be administered intravenously, parenterally, orally, nasally, by inhalation, by implant, by injection, or by suppository. The composition can be administered in a single dose or in more than one dose over a period of time to confer the desired effect.

The actual effective amounts of drug of the present invention can vary according to the specific drug being utilized, the particular composition formulated, the mode of administration and the age, weight and condition of the patient, for example. As used herein, an effective amount of an ICAM antagonist is an amount of the drug which is capable of reducing the edema and/or ischemia levels. Dosages for a particular patient can be determined by one of ordinary skill in the art using conventional considerations, (e.g. by means of an appropriate, conventional pharmacological protocol).

Exemplification

EXAMPLE 1

Prevention of Leukostasis and Vascular Leakage Diabetic Retinopathy via ICAM-1 Inhibition Diabetic retinopathy is a leading cause of adult vision loss and blindness. Much of the retinal damage that characterizes the disease results from retinal vascular leakage and non-perfusion. This study demonstrates that diabetic retinal vascular leakage and non-perfusion are temporally and spatially associated with retinal leukocyte stasis (leukostasis) in the rat model of streptozotocin-induced diabetes. Retinal leukostasis increases within days of developing diabetes and correlates with the increased expression of retinal intercellular adhesion molecule-i (ICAM-1). ICAM-1 blockade with a monoclonal antibody prevents diabetic retinal leukostasis (e.g., resulting in ischemia) and vascular leakage (e.g., resulting in edema) by 48.5% and 85.6%, respectively. These data identify the causal role of leukocytes in the pathogenesis of diabetic retinopathy and demonstrate the important utility of ICAM-1 inhibition as a therapeutic strategy for the prevention of diabetic retinopathy.

While retinal vascular leakage and non-perfusion are recognized as two major complications of diabetes, their pathogenesis remains poorly understood. Leukocytes may be involved in the genesis of these complications. Diabetic retinopathy is not generally considered an inflammatory disease, yet the retinal vasculature of humans and rodents with diabetes mellitus contains increased numbers of leukocytes. Many of these leukocytes are static. The causes and consequences of this phenomenon are largely unknown. Intercellular adhesion molecule-1 (ICAM-1) is a peptide that mediates leukocyte adhesion and transmigration. ICAM-1 may be operative in the stasis observed in diabetic retinopathy because ICAM-1 immunoreactivity is increased in the diabetic retinal vasculature of humans. However, little is known about the direct pathogenetic role of ICAM-1 in diabetic retinopathy. This study investigated the mechanisms of diabetic retinal leukocyte stasis (leukostasis) and the role leukocytes play in the development of two sight-threatening complications, vascular leakage and capillary non-perfusion.

Experimental Procedures

Animals and Experimental Diabetes. Long-Evans rats weighing approximately 200 g received a single 60 mg/kg injection of streptozotocin (Sigma, St. Louis, Mo.) in 10 mM citrate buffer, pH 4.5, after an overnight fast. Control non-diabetic animals received citrate buffer alone. Animals with blood glucose levels greater than 250 mg/dl 24 hours later were considered diabetic. Blood pressure was measured using a noninvasive cuff sensor and monitoring system (Ueda Electronics, Tokyo, Japan). Blood anticoagulated with EDTA was drawn from the abdominal aorta of each rat after the experiment. The blood sample was analyzed using a hematology analyzer. The rats were fed on standard laboratory chow and were allowed free access to water in an air-conditioned room with a 12-hour light-12-hour dark cycle until they were used for the experiments.

Acridine Orange Leukocyte Fluorography (AOLF) and Fluorescein Angiography. Leukocyte dynamics in the retina were studied with AOLF (Miyamoto, K., et al., *Invest. Ophthalmol. Vis. Sci.*, 39:2190–2194 (1998); Nishiwaki, H., et al., *Invest. Ophthalmol. Vis. Sci.*, 37:1341–1347 (1996); Miyamoto, K., et al., *Invest. Ophthalmol. Vis. Sci.*, 37:2708–2715 (1996)). Intravenous injection of acridine orange causes leukocytes and endothelial cells to fluoresce through the non-covalent binding of the molecule to double stranded nucleic acid. When a scanning laser ophthahnoscope is utilized, retinal leukocytes within blood vessels can be visualized in vivo. Twenty minutes after acridine orange injection, static leukocytes in the capillary bed can be observed. Immediately after observing and recording the static leukocytes, fluorescein angiography was performed to study the relationship between static leukocytes and retinal vasculature.

Twenty-four hours before AOLF and fluorescein angiography were performed, all rats had a heparin-lock catheter surgically implanted in the right jugular vein for the administration of acridine orange or sodium fluorescein dye. The catheter was subcutaneously externalized to the back of the neck. The rats were anesthetized for this procedure with xylazine hydrochloride (4 mg/kg) (Phoenix Pharmaceutical, St. Joseph, Mo.) and ketamine hydrochloride (25 mg/kg) (Parke-Davis, Morris Plains, N.J.). Immediately before AOLF, each rat was again anesthetized, and the pupil of the left eye was dilated with 1% tropicamide (Alcon, Humancao, Puerto Rico) to observe leukocyte dynamics. A focused image of the peripapillary fundus of the left eye was obtained with a scanning laser ophthalmoscope (SLO; Rodenstock Instrument, Munich, Germany). Acridine orange (Sigma, St. Louis, Mo.) was dissolved in sterile saline (1.0 mg/ml) and 3 mg/kg was injected through the jugular vein catheter at a rate of 1 ml/min. The fundus was observed with the SLO using the argon blue laser as the illumination source and the standard fluorescein angiography filter in the 40° field setting for 1 minute. Twenty minutes later, the fundus was again observed to evaluate leukostasis in the retina. Immediately after evaluating retinal leukostasis, 20 μl of 1% sodium fluorescein dye was injected into the jugular vein catheter. The images were recorded on a videotape at the rate of 30 frames/sec. The video recordings were analyzed on a computer equipped with a video digitizer (Radius, San Jose, Calif.) that digitizes the video image in real time (30 frames/sec) to 640×480 pixels with an intensity resolution of 256 steps. For evaluating retinal leukostasis, an observation area around the optic disc measuring ten disc diameters in diameter was determined by drawing a polygon surrounded by the adjacent major retinal vessels. The area was measured in pixels and the density of trapped leukocytes was calculated by dividing the number of trapped leukocytes, which were recognized as fluorescent dots, by the area of the observation region. The densities of leukocytes were calculated generally in eight peripapillary observation areas and an average density was obtained by averaging the eight density values.

Isotope Dilution Technique. Vascular leakage was quantified using an isotope dilution technique based on the injection of bovine serum albumin (BSA) labeled with two different iodine isotopes, $^{125}$I and $^{131}$I. Briefly, purified monomer BSA (1 mg) was iodinated with 1 mCi of $^{131}$I or $^{125}$I using the iodogen method. Polyethylene tubing (0.58 mm internal diameter) was used to cannulate the right jugular vein and the left or right iliac artery. The tubing was filled with heparinized saline. The right jugular vein cannula was used for tracer injection. The iliac artery cannula was connected to a one ml syringe attached to a Harvard Bioscience model PHD 2000 constant-withdrawal pump preset to withdraw at a constant rate of 0.055 ml/min. At time 0, [$^{125}$I]BSA (50 million cpm in 0.3 ml of saline) was injected into the jugular vein and the withdrawal pump started. At the eight-minute mark, 0.2 ml (50 million cpm) of [$^{131}$I]BSA was injected. At the ten-minute mark, the heart was excised, the withdrawal pump was stopped, and the retina was quickly dissected and sampled for g-spectrometry. Tissue and arterial samples were weighed and counted in a g-spectrometer (Beckman 5500, Irvine, Calif.). The data were corrected for background and a quantitative index of [$^{125}$I]BSA tissue clearance was calculated as previously described and expressed as μg plasma ×g tissue wet weight$^{-1}$×min$^{-1}$. Briefly, [$^{125}$I]BSA tissue activity was corrected for [$^{1251}$I]BSA contained within the tissue vasculature by multiplying [$^{125}$I]BSA activity in the tissue by the ratio of [$^{125}$I]BSA/[$^{131}$I]BSA in the arterial plasma sample obtained at the end of the experiment. The vascular-corrected [$^{125}$I] BSA activity was divided by the time-averaged [$^{125}$I]BSA plasma activity (obtained from a well-mixed sample of plasma taken from the withdrawal syringe) and by the tracer circulation time (10 minutes) and then normalized per gram tissue wet weight.

Ribonuclease Protection Assay. The retinas were gently dissected free and cut at the optic disc after enucleation, and frozen immediately in liquid nitrogen. Total RNA was isolated from rat retinas according to the acid guanidinium thiocyanate-phenol-chloroform extraction method. A 425-base pair EcoRI/BamHI fragment of rat ICAM-1 cDNA was prepared by reverse transcription-polymerase chain reaction and cloned into pBluescript II KS vector. A 472 nucleotide antisense riboprobe was prepared by in vitro transcription (Promega, Madison, Wis.) of linearized plasmid DNA with T7 RNA polymerase in the presence of [$^{32}$P]dUTP. The sequence of the cloned cDNA was verified by DNA sequencing. Twenty micrograms of total cellular RNA were used for ribonuclease protection assays. All samples were simultaneously hybridized with an 18S riboprobe (Ambion, Austin, Tex.) to normalize for variations in loading and recovery of RNA. Protected fragments were separated on a gel of 5% acrylamide, 8M urea, 1x Tris-borate-EDTA, and quantified with a PhosphorImager (Molecular Dynamics, Sunnyvale, Calif.).

ICAM-1 Blockade. Twenty four hours following streptozotocin injection, confirmed diabetic animals received intraperitoneal injections of 3 mg/kg or 5 mg/kg rat ICAM-1 neutralizing antibody (1A29; R&D Systems, Minneapolis Minn.) or 5 mg/kg normal mouse IgG1 (R&D Systems) in sterile phosphate buffered saline. The animals were treated three times per week. Retinal leukostasis and vascular leakage were studied one week following diabetes induction.

Statistical Analysis. All results are expressed as means±SD. The data were compared by analysis of variance (ANOVA) with post-hoc comparisons tested using Fisher's protected least significant difference (PLSD) procedure. Differences were considered statistically significant when P values were less than 0.05.

Results and Discussion

Time-Course Changes of Retinal Leukostasis and Vascular Leakage after Diabetes Induction. Retinal leukostasis was quantified in Long-Evans rats. Diabetic rats, like humans with diabetes, develop retinal non-perfusion and increased vascular permeability. FIG. 1 shows the time course of diabetic retinal leukostasis and vascular leakage. In FIG. 1A, leukostasis was serially quantified using AOLF. Non-diabetic animals (day 0) and animals with streptozotocin-induced diabetes of varying duration were studied. Using AOLF, a time course analysis showed that retinal leukostasis increased 1.9-fold as early as three days following diabetes induction (n=5, p<0.05) (FIG. 1A). After one week of diabetes, retinal leukostasis was 3.2-fold higher than in non-diabetic controls (n=5, p<0.0001). This finding remained unchanged in degree for three additional weeks (n=5, p<0.0001) (FIG. 1A). Reliable leukostasis quantitation beyond the four-week time point was precluded by cataract formation.

Figure 1B:
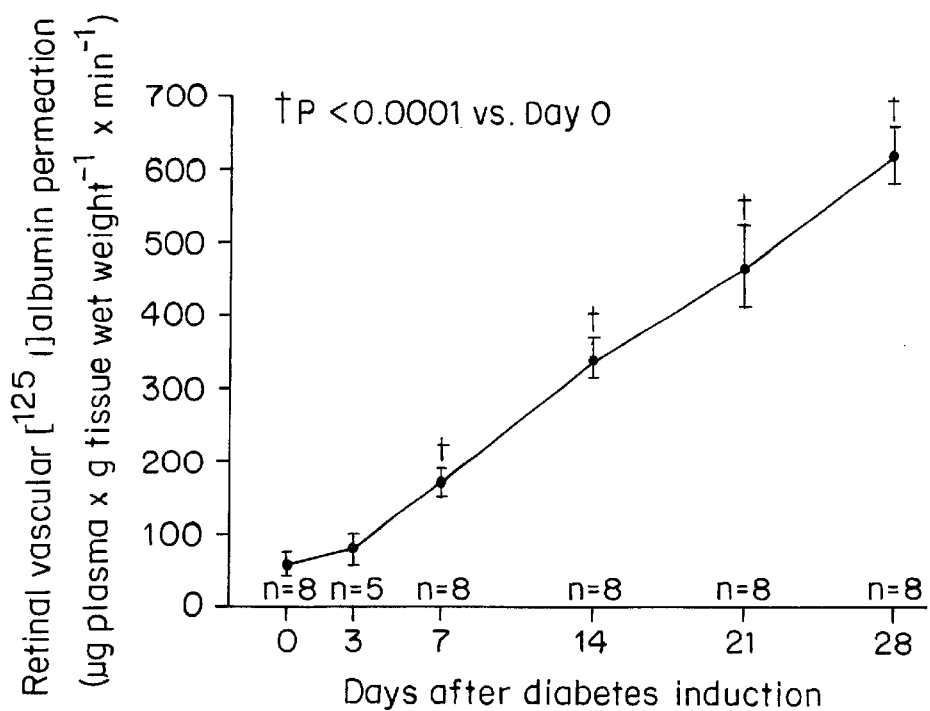
FIG. 1B is a graph showing the retinal vascular [$^{125}$I] albumin permeation measured 0, 3, 7, 14, 21 and 28 days after diabetes induction. The graph shows a time course of vascular leakage. All data show the mean±the standard deviation (SD).

Leukocyte adhesion to endothelial cells can trigger the disorganization of endothelial cell adherens and tight junctions and vascular leakage. To determine if diabetic retinal leukostasis was correlated with blood-retinal barrier breakdown, retinal albumin permeation was quantified (FIG. 1B). In FIG. 1B, radioactive albumin permeation into retinal tissue was quantitated at the same time points using the isotope dilution technique. Retinal albumin permeation characterizes human and rodent diabetic retinopathy and can be sensitively quantified using the isotope dilution technique (Tilton, R. G., et al., *Diabetes* 42:221–232 (1993); Tilton, R. G., et al., *J. Clin. Invest.* 99:2192–2202 (1997); and Vinores, S. A., et al., *Am. J. Pathol.*, 134:231–235 (1989). A time course analysis in diabetic rats revealed a 2.9-fold (n=8, p<0.0001) and 10.7-fold (n=8, p<0.0001) increase in albumin permeation following one and four weeks of diabetes (FIG. 1B). The breakdown of the blood-retinal barrier followed the onset of diabetes-associated retinal leukostasis.

Figure 2A:
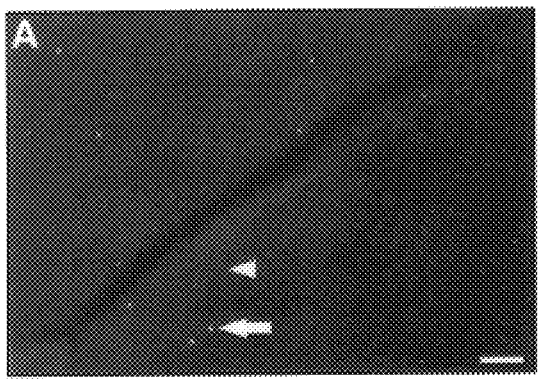
FIGS. 2A–D show four photographs of the same retinal area.
Figure 2B:
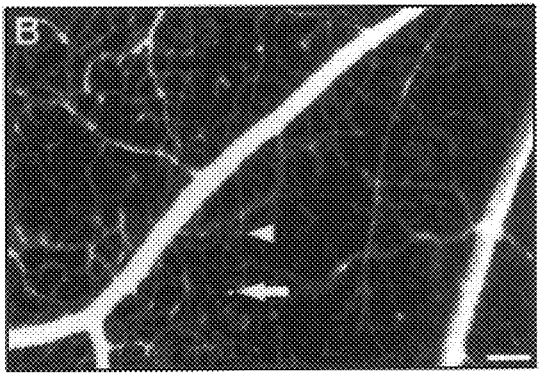
Figure 2C:
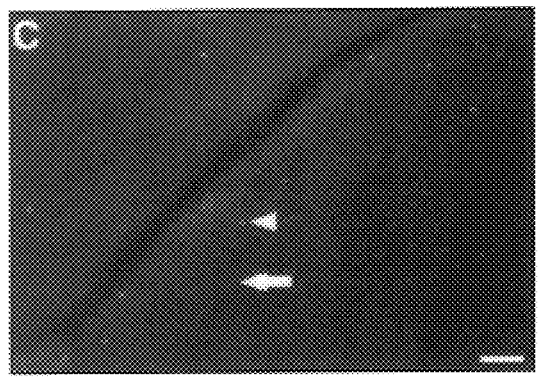
Figure 2D:
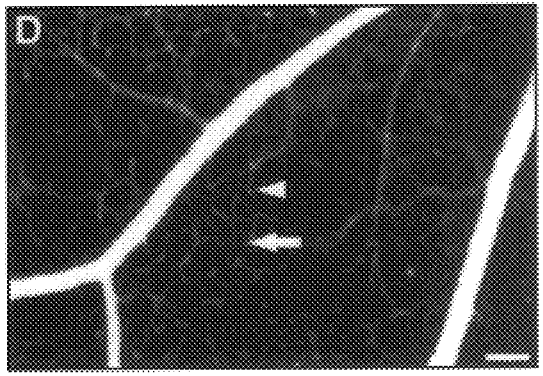

Leukocyte-Induced Non-perfusion and Reperfusion in Retinal Capillaries. To further characterize the diabetic retinal leukostasis, serial AOLF and fluorescein angiography studies were performed. FIG. 2 shows that static leukocytes are in flux, block capillary flow and transmigrate. Serial AOLF of static leukocytes in the same retinal area after seven (FIG. 2A) and eight (FIG. 2C) days of diabetes shows their complete replacement within a 24 hour period. The arrow points to a static leukocyte (FIGS. 2A and 2B) that appears to have transmigrated (FIG. 2B). One day later, AOLF and fluorescein angiography show that the leukocyte has disappeared (FIGS. 2C and 2D). The arrowhead shows a patent capillary (FIG. 2B) that subsequently becomes obstructed by a static leukocyte 24 hours later (FIGS. 2C and 2D). These studies revealed that the individual leukocytes observed with AOLF are in flux, even though the overall degree of leukostasis is constant (FIG. 2). The static retinal leukocytes observed seven days following the induction of diabetes are topographically distinct from those observed 24 hours later. Furthermore, a fraction of the leukocytes are in the extravascular space, a result consistent with their rapid transmigration following dye labeling.

Figure 3A:
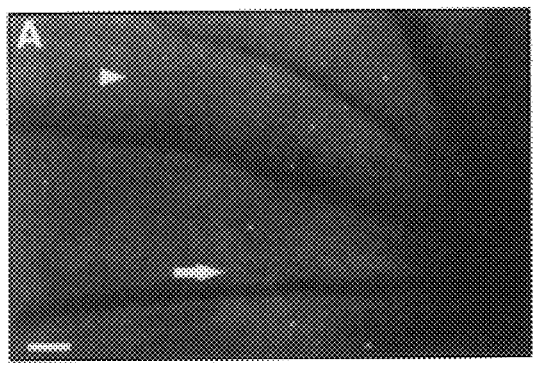
FIGS. 3A–F show six photographs of a retinal area.
Figure 3B:
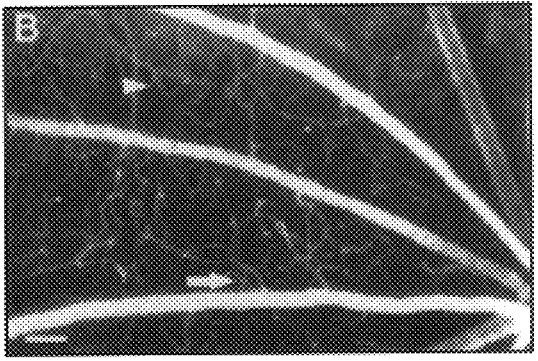
Figure 3C:
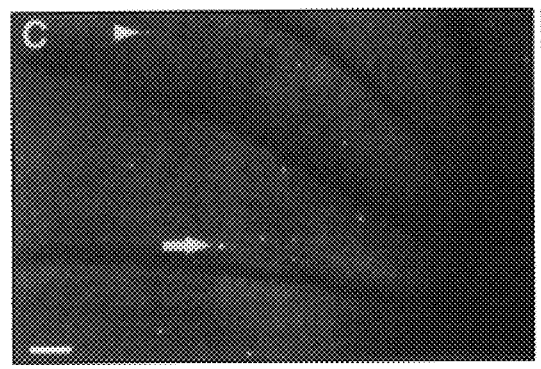
Figure 3D:
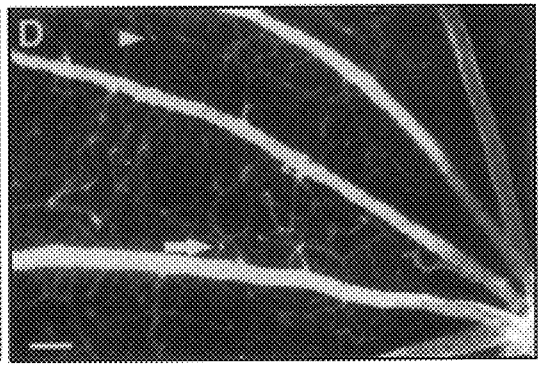
Figure 3E:
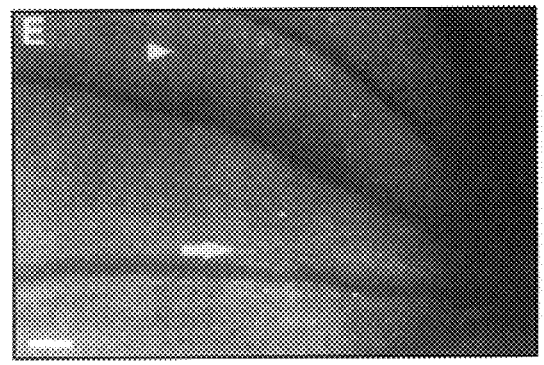
Figure 3F:
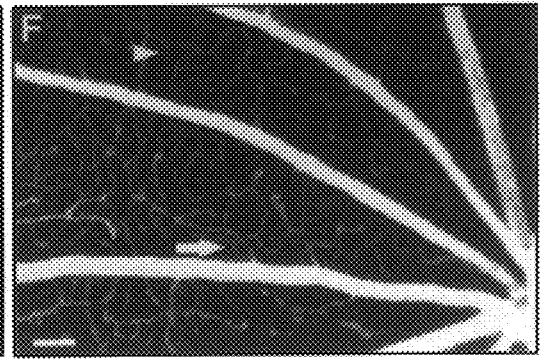

Fluorescein angiography and AOLF were also used to study retinal non-perfusion. These studies identified static leukocytes directly associated with areas of downstream non-perfusion (FIGS. 2 and 3). FIG. 3 shows leukocyte-induced non-perfusion and reperfusion. Serial studies were completed one (FIGS. 3A and 3B), two (FIGS. 3C and 3D) and four (FIGS. 3E and 3F) weeks following diabetes induction using both AOLF (FIGS. 3A, 3C, and 3E) and fluorescein angiography (FIGS. 3B, 3D, and 3F). The arrow shows a patent capillary (FIG. 3B) that subsequently becomes occluded downstream from a static leukocyte (FIGS. 3C and 3D), and then opens up when the leukocyte disappears (FIGS. 3E and 3F). The arrowhead shows a patent capillary (FIG. 3B) that becomes occluded downstream from a static leukocyte (FIGS. 3C and 3D) and then remains closed after the leukocyte has disappeared (FIGS. 3E and 3F). The non-perfused capillaries were patent prior to the onset of the leukostasis, indicating a causal relationship. As the leukocyte(s) disappeared, the capillaries either reperfused or remained closed (FIG. 3). Reperfusion has been observed in human diabetic retinopathy, but the mechanism, until now, has remained unexplained.

Figure 4A:
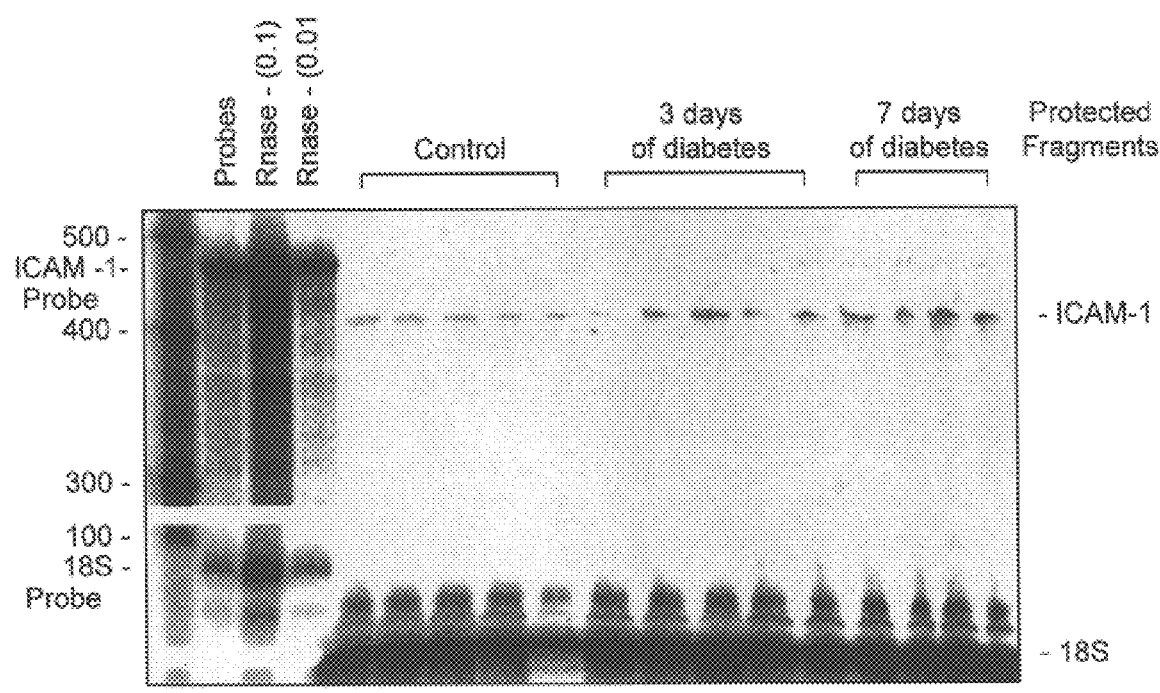
FIG. 4A is a photograph of ribonuclease protection assay results showing ICAM-1 mRNA levels from controls and a diabetic rat three days following diabetes induction. Each lane is the signal from the two retinas of a single animal. The lane labeled "Probes" shows a hundred-fold dilution of the full-length ICAM-1 and 18S riboprobes. The lanes labeled "RNase-(0.1)" and "RNase-(0.01)" show the ten-fold and hundred-fold dilutions, respectively, of the full length riboprobes without sample or RNase.
Figure 4B:
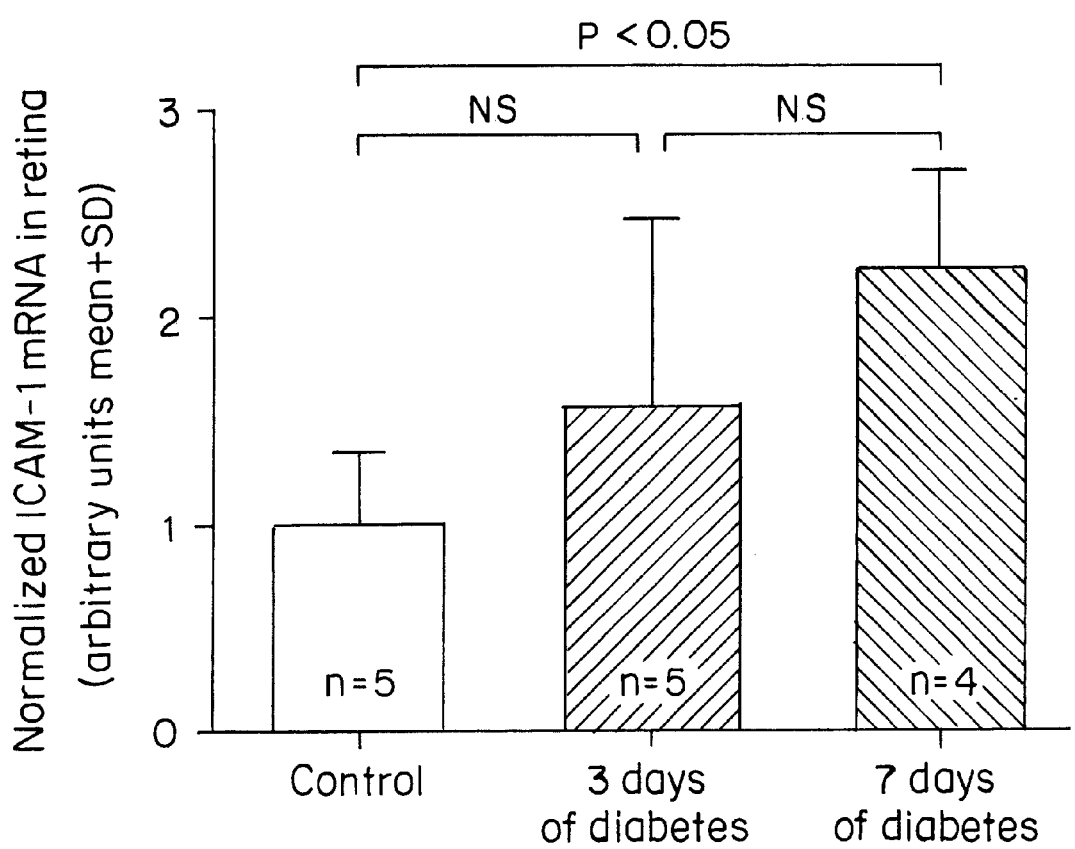
FIG. 4B is a bar graph showing units of normalized ICAM-1 mRNA for controls, three days and seven days after diabetes induction.
Figure 5A:
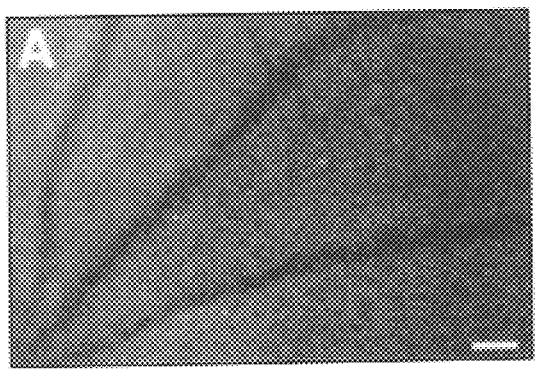
FIGS. 5A–D are photographs of the retinal area. The representative retinal leukostasis is shown in non-diabetic test subjects (FIG. 5A), diabetic test subjects (FIG. 5B), diabetic test subjects given 5 mg/kg mouse control IgG1 (FIG. 5C) and diabetic test subjects treated with 5 mg/kg anti-ICAM-1 mAb-treated animals (FIG. 5D). Scale Bars= 100 μm; 3.2 pixel=1 μm.
Figure 5B:
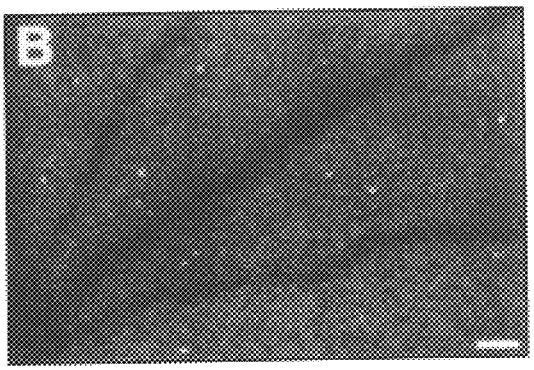
Figure 5C:
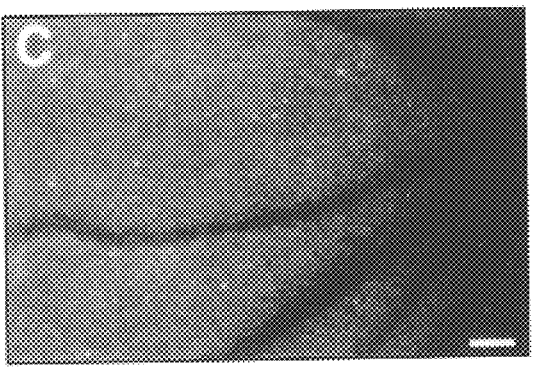
Figure 5D:
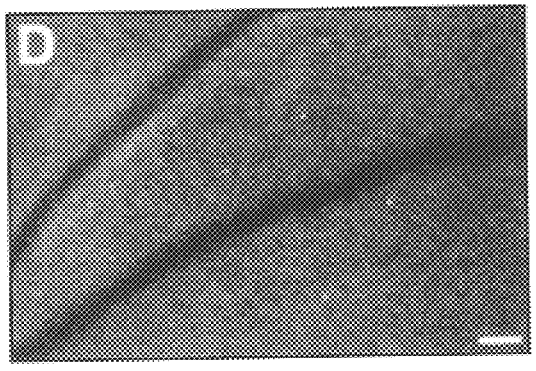

FIG. 4A shows results from a ribonuclease protection assay, which demonstrates that retinal ICAM-1 levels were significantly increased seven days following diabetes induction. Each lane shows the signal from the two retinas of a single animal. The lane labeled "Probes" shows a hundred-fold dilution of the full-length ICAM-1 and 18S riboprobes. The lanes labeled "RNase-(0.1)" and "RNase-(0.01)" show the ten-fold and hundred-fold dilutions, respectively, of the full-length riboprobes without sample or RNase. When normalized to 18S RNA, the retinal ICAM-1 levels after seven days of diabetes were 2.2-fold higher (n=4, p<0.05) than in the non-diabetic controls (FIG. 4B). Retinas analyzed three days following diabetes induction demonstrated that retinal ICAM-1 IMRNA levels were 1.5-fold higher than non-diabetic controls, but this increase was not statistically significant (n=5, p>0.05) (FIG. 4). After one week of diabetes, the retinal ICAM-1 levels were 2.2-fold greater, a significant increase when compared to non-diabetic controls (n=4, p<0.05). The ICAM-1 increase coincided temporally with the development of diabetic retinal leukostasis and blood-retinal barrier breakdown.

Figure 6A:
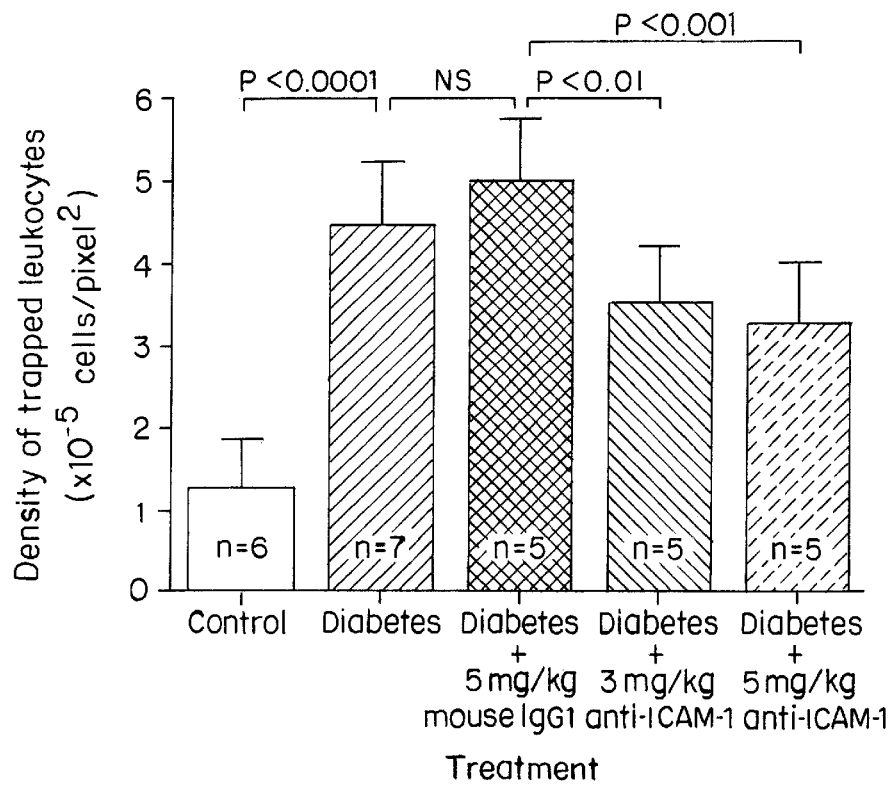
FIG. 6A is a bar graph showing the density of trapped leukocytes ($\times 10^{-5}$ cells/pixel$^2$) for control, diabetic test subjects not given anything, diabetic test subjects given 5 mg/kg mouse IgG1, diabetic test subjects treated with 3 mg/kg anti-ICAM-1 antibody, and diabetic test subjects treated with 5 mg/kg anti-ICAM-1 antibody. NS=Not Significant.

An Anti-ICAM-1 Monoclonal Antibody (mAb) Prevents Leukostasis and Vascular Leakage in Diabetic Retina. To assess whether ICAM-1 mediates diabetic retinal leukostasis, a well characterized ICAM-1 neutralizing antibody (IA29) was used for in vivo adhesion blockade experiments. Tamatani, T. et al., *Int. Immunol.* 2, 165–171 (1990); Kawasaki, K., et al., *J. Immunol.* 150, 1074–1083 (1993); Kelly, K. et al., *Proc. Natl. Acad. Sci.* USA 91, 812–816 (1994). Animals received either 3 or 5 mg/kg intraperitoneal injections of the ICAM-1 antibody three times weekly. Control diabetic animals received an equivalent amount of a non-immune isotype control antibody. All animals were analyzed one week following diabetes induction. The results showed that the ICAM-1 antibody blocked diabetes-induced leukostasis by 40.9% (3 mg/kg, n=5, p<0.01) and 48.5% (5 mg/kg, n=5, p<0.001) (FIGS. 5 and 6A). The peripheral leukocyte counts at one week increased by 40% (5 mg/kg, n=5, p<0.05) compared to the control antibody treated animals, a result consistent with successful systemic ICAM-1 blockade (Table 1). Body weight, plasma glucose and blood pressure were unchanged in all diabetic groups (Table 1).

TABLE 1

Characteristics of control, diabetic, mouse IgG1-treated diabetic, and anti-ICAM-1 mAb-treated diabetic rats

|  | Control | Diabetes | Diabetes + 5 mg/kg mouse IgG1 | Diabetes + anti-ICAM-1 mAb | |
|---|---|---|---|---|---|
|  |  |  |  | 3 mg/kg | 5 mg/kg |
| n | 6 CR | 7 | 5 | 5 | 5 |
| Body weight (g) | 271 ± 12 | 240 ± 12* | 235 ± 9* | 238 ± 6* | 239 ± 12* |
| Plasma glucose (mg/dl) | 123 ± 19 | 332 ± 35* | 316 ± 61* | 351 ± 83* | 373 ± 68* |
| Blood Pressure (mmHg) | 111 ± 6 | 104 ± 12 | 109 ± 14 | 105 ± 9 | 105 ± 10 |
| Leukocyte count (×$10^3$/µl) | 6.1 ± 1.6 | 5.0 ± 1.5♦ | 5.3 ± 0.8♦ | 6.9 ± 1.4 | 7.4 ± 2.3 |

ICAM-1 Gene Expression in Diabetic Retina. To determine if retinal ICAM-1 expression increases in association with diabetic retinal leukostasis, ICAM-1 mRNA levels were quantified using the ribonuclease protection assay. FIG. 4 shows ICAM-1 gene expression in diabetic retina.

Values are means±SD. ★P<0.0001 vs. control rats; ♦P<0.05 vs. 5 mg/kg anti-ICAM-1 mAb-treated diabetic rats. All results are expressed as means±SD. Unpaired groups of two were compared using two sample t-test or two sample t-test with Welch's correction. To compare three or more groups, analysis of variance was followed by the post hoc test with Fisher's PLSD procedure. Differences were considered statistically significant when P values were less than 0.05.

Figure 6B:
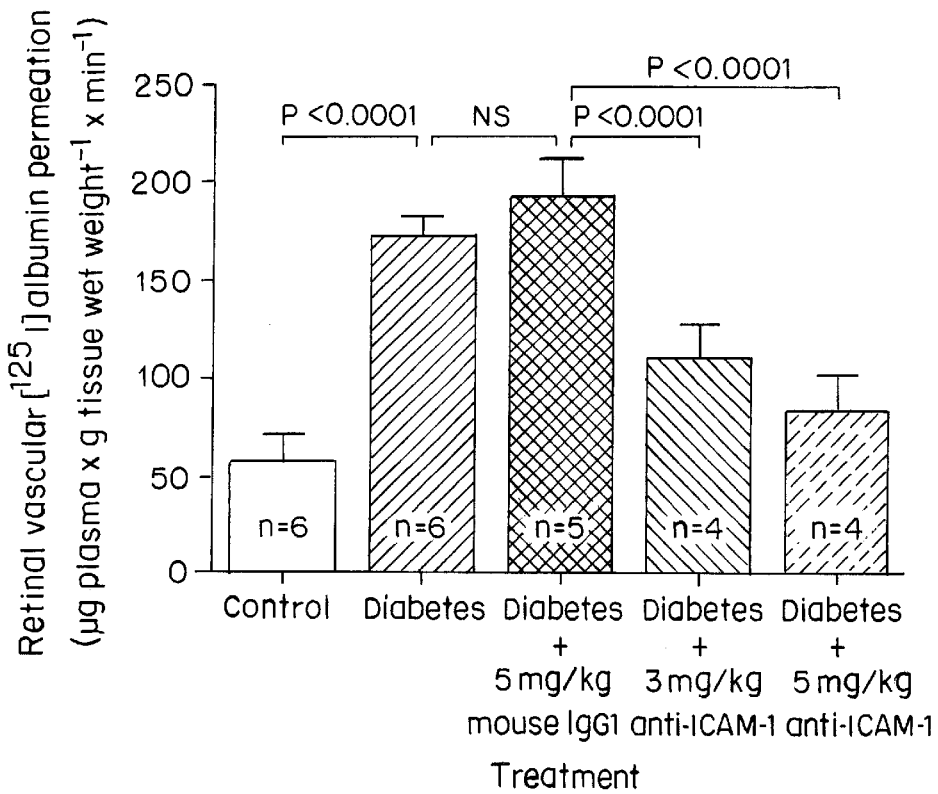
FIG. 6B is a bar graph showing the retinal vascular $^{125}$I albumin permeation (μg plasma×g tissue wet weight$^{-1}$×min$^{-1}$) for control, diabetic test subjects not given anything, diabetic test subjects given 5 mg/kg mouse IgG1, diabetic test subjects treated with 3 mg/kg anti-ICAM-1 antibody, and diabetic test subjects treated with 5 mg/kg anti-ICAM-1 antibody. NS=Not Significant.

The effect of the ICAM-1 inhibition on blood-retinal barrier breakdown was tested using the same antibody. Animals receiving 3 and 5 mg/kg of the anti-ICAM-1 antibody had 63.5% (3 mg/kg, n=4, p<0.0001) and 85.6% (5 mg/kg, n=4, p<0.0001) less retinal albumin permeation at one week (FIG. 6B). The results suggest that the ICAM-1-dependent component of the leukostasis is largely responsible for the blood-retinal barrier breakdown.

EXAMPLE 2

Integrin-Mediated Neutrophil Adhesion and Retinal Leukostasis in Diabetes

Introduction:

Leukocyte-endothelial cell interactions in tissues are mediated by adhesion molecules expressed on the surface of leukocytes and endothelial cells. Immunoglobulin superfamily molecules such as ICAM-1 are expressed on endothelial cells and bind to $\beta_2$-integrins expressed on leukocytes. The integrins are transmembrane receptors that consist of noncovalently bound heterodimers composed of $\alpha$ and $\beta$-chains. The $\beta_2$-integrins are operative in leukocyte adhesion and include LFA-1 (lymphocyte function associated antigen, CD11a/CD18), Mac-1 (leukocyte adhesion receptor, CD11b/CD18) and p150/95 (CD11 c/CD18). Each of the $\beta_2$-integrins has a common $\beta$-chain in combination with a unique $\alpha$-chain. CD18 is required for the firm attachment of healthy human neutrophils to human umbilical vein endothelial cells.

In vivo studies from our laboratory have investigated the role of leukocytes in diabetic retinopathy. Utilizing acridine orange leukocyte fluorography, the density of static leukocytes in the retinas of streptozotocin-induced diabetic rats was demonstrated to be increased. Retinal leukocyte stasis (leukostasis) was observed within three days of diabetes induction, and was temporally and spatially correlated with capillary non-perfusion and blood-retinal barrier breakdown. The onset of retinal leukostasis coincided with the upregulation of retinal ICAM-1 expression. Causality was demonstrated when an anti-ICAM-l antibody prevented the diabetes-associated increases in retinal leukostasis and vascular leakage by 48.5% and 85.6%, respectively. However the identities and bioactivities of the neutrophil adhesion molecules mediating diabetic retinal leukostasis are less well understood.

The aim of the current study was to investigate in greater detail the role of neutrophils in early diabetic retinal leukostasis. A time point of one week of diabetes was chosen in this study because steady-state increases in diabetic retinal leukostasis and ICAM-1 expression are achieved in one week. Since adhesion can occur in the absence of increased adhesion molecule expression, both adhesion molecule expression and bioactivity were examined. Finally, the role of CD18 in the development of diabetic retinal leukostasis was examined in vivo using acridine orange leukocyte fluorography and neutralizing anti-CD18 F(ab')$_2$ fragments.

Methods

Diabetes was induced in Long Evans rats with streptozotocin. The expression of the surface integrin subunits CD11a, CD11b, and CD18 on rat neutrophils isolated from peripheral blood was quantitated with flow cytometry. In vitro neutrophil adhesion was studied using quantitative endothelial cell-neutrophil adhesion assays. The adhesive role of the integrin subunits CD11a, CD11b and CD18 was tested using specific neutralizing monoclonal antibodies. CD18 bioactivity was blocked in vivo with anti-CD18 F(ab')$_2$ fragments and the effect on retinal leukocyte adhesion was quantitated with acridine orange leukocyte fluorography (AOLF).

Animals

Male Long-Evans rats weighing approximately 200 g were used for these experiments. The rats were fed standard laboratory chow and allowed free access to water in an air-conditioned room with a 12-hour light-12-hour dark cycle.

Induction of Diabetes

Rats received a single 60 mg/kg intraperitoneal injection of streptozotocin (Sigma, St. Louis, Mo.) in 10 mM sodium citrate buffer, pH 4.5, after an overnight fast. Control non-diabetic animals received citrate buffer alone. Animals with blood glucose levels greater than 250 mg/dl 24 hours after injection were considered diabetic. All experiments were performed one week following the induction of diabetes.

Monoclonal Antibodies and F(ab')2 Fragments

The monoclonal antibodies (mAb) were murine in origin and were used as purified IgG. For the in vitro studies, mAbs WT.1 (anti-rat CD11a), 6G2 (anti-rat CD18), and MRC OX-42 (anti-rat CD11b) were obtained from Serotec Inc. (Raleigh, N.C.). FITC-conjugated mouse IgG, mAb isotype control was obtained from PharMingen (San Diego, Calif.). Fluorescein isothiocyanate (FITC)-conjugated goat anti-mouse IgG, Ab was obtained from Caltag Laboratories (Burlingame, Cailf.). For the in vivo studies, WT.3 anti-rat LFA-1 beta chain (CD18) F(ab')$_2$ fragments were obtained from Seikagaku America (Division of Associates of Cape Cod, Inc., Falmouth, Mass.). Purified mouse anti-human IgG F(ab')$_2$ fragments were obtained from Jackson ImmunoResearch Laboratories Inc. (West Grove, Pa.).

Flow Cytometry

The surface expression of CD11a, CD11b, and CD18 on rat neutrophils was determined using flow cytometry as previously described. Allport JR, et al., *J. Immunol.*, 158:4365–4372 (1997). Briefly, whole blood anticoagulated with EDTA was obtained from the hearts of rats anesthetized with inhaled isofluorane. Leukocytes were isolated by dextran sedimentation and hypotonic lysis of contaminating erythrocytes. Aliquots of $5 \times 10^5$ cells in 100 $\mu$l RPMI 1640 medium (Bio Whittaker, Walkersville, Md.) containing 5% fetal bovine serum (RPMI-5%) were incubated on ice for 10 min. The tubes were centrifuged at 400×g for 5 min at 4° C. The cell pellets were resuspended in 100 $\mu$l RPMI-5% containing 20 $\mu$g/ml primary mAb to CD11a, CD11b, CD18 or isotype control and incubated for 45 min on ice. Primary mAb were detected with FITC-conjugated goat anti-mouse IgG$_1$ Ab as previously detailed. The fluorescence of 104 cells was measured on a FACScan (Becton Dickinson, San Jose, Calif.). Neutropffils were manually gated on the basis of their characteristic forward and side light scattering properties. The surface expression is presented as the mean channel fluorescence on a logarithmic scale.

Endothelial Cell-Neutrophil Adhesion Assays

Peripheral blood was obtained from rats anesthetized with inhaled isofluorane via heart puncture with a 16-gauge EDTA flushed needle. Neutrophils were isolated from whole blood by density gradient centrifugation with NIM·2™ (Neutrophil Isolation Media; Cardinal Associates, Santa Fe, N.Mex.) according to the manufacturer's instructions. Preparations contained >94% neutrophils as determined by eosin and methylene blue staining (Leukostat staining system; Fischer Scientific, Pittsburgh, Pa.). There was no red blood cell contamination. The cells were used immediately after collection.

The adhesion of unstimulated neutrophils to confluent monolayers of rat prostate endothelial cells (RPEC) was determined under static conditions as previously described. (Luscinskas F W, et al., *JImmunol.*, 149:2163 (1992); Kiely J M, et al., "Methods in Molecular Biology, Adhesion Protein Protocols," Leukocyte-endothelial monolayer adhesion assay (static conditions), 131–136 (1999). RPEC were obtained from the American Type Culture Collection (ATCC; Manassas, Va.) and cultured in Eagle's minimum essential media (ATCC) supplemented with 5% fetal bovine serum (FBS; GIBCO, Gaithersburg, Md.) and 0.3 ng/ml porcine intestinal heparin (Sigma, St. Louis, Mo.). RPEC were grown to confluence on tissue culture-treated plastic microtiter 96-well plates, stimulated for 24-hours with 30 ng/ml recombinant human TNF-α (Genzyme Corp., Cambridge, Ma.), and incubated for 15 minutes with RPMI-5%. TNF-α stimulation of ICAM-1 surface expression was utilized for all experiments. Neutrophils were resuspended at 2×106 cells/ml in RPMI-5% and incubated for 10 min at 37° C. with 1 $\mu$M of the fluorescent marker, 2', 7'-bis-(2-carboxyethyl)-5 (and 6) carboxyfluorescein, acetoxymethyl ester (Molecular Probes, Eugene, Oreg.) in DMSO (vehicle). Fluorescent labeled neutrophils were washed once and then incubated in RPMI-5% alone or RPMI-5% with a saturating concentration of mAb (30 pg/ml) to CD11a, CD11b, or CD18 for 10 min at room temperature. The neutrophils were washed and then incubated (2×10$^6$ neutrophils/ml, 50 $\mu$l per well) with RPEC for 10 min at 37° C. Non-adherent cells were removed and the content of the wells lysed with 10 mM Tris-HCl, pH 8.4 containing 0.1% SDS. Fluorescence was determined in a microtiter plate fluorimeter (excitation 485 nm, emission 530–540 nm) and the adhesion reported as the number of adherent neutrophils/nm$^2$.

Acridine Orange Leukocyte Fluorography (AOLF)

Leukocyte dynamics in the retina were studied with AOLF. (Miyamoto, K., et al., "In vivo demonstration of increased leukocyte entrapment in retinal microcirculation of diabetic rats," *Invest Opthalmol Vis Sci.*, 39:2190–2194 (1998); Miyamoto, K., et al., *Proc Natl Acad Sci USA*, 96(19):10836–41 (1999); Nishiwaki, H., et al., *Invest Ophthalmol Vis Sci.*, 36:123–130 (1995); Nishiwaki, H., et al., *Invest Ophthalmol Vis Sci.*, 37:1341–1347 (1997)). Rats were anesthetized with 4 mg/kg xylazine hydrochloride (Phoenix Pharmaceutical, St. Joseph, Mo.) and 25 mg/kg ketamine hydrochloride (Parke-Davis, Morris Plains, N.J.). The day before leukocyte dynamics were observed, a heparin-lock catheter was surgically implanted in the right jugular vein of each rat. The catheter was subcutaneously externalized to the back of the neck. Rats received intravenous injections of 5 mg/kg anti-rat beta chain (CD18, WT.3) F(ab')$_2$ fragments or 5 mg/kg anti-human IgG isotype control F(ab')$_2$ fragments in sterile phosphate buffered saline 24 hours before AOLF was performed. The experiments were carried out in a masked fashion.

Immediately before AOLF, each rat was again anesthetized, and the pupil of the left eye was dilated with 1% tropicamide (Alcon, Humancao, Puerto Rico) to observe leukocyte dynamics. A focused image of the peripapillary fundus of the left eye was obtained with a scanning laser ophthalmoscope (SLO; Rodenstock Instruments, Munich, Germany). Acridine orange (Sigma, St. Louis, Mo.) was dissolved in sterile saline (1.0 mg/ml) and 3 mg/kg was injected through the jugular vein catheter at a rate of 1 ml/min. The fundus was observed with the SLO using the argon blue laser as the illumination source and the standard fluorescein angiography filter in the 400 field setting for 1 min. Twenty min later, the fundus was again observed to evaluate leukostasis in the retina. The images were recorded on videotape at the rate of 30 frames/sec. The video recordings were analyzed on a computer equipped with a video digitizer (Radius, San Jose, Calif.) that digitizes the video image in real time (30 frames/sec) to 640×480 pixels with an intensity resolution of 256 steps. For evaluating retinal leukostasis, an observation area around the optic disc measuring five disc diameters in radius was determined by drawing a polygon bordered by the adjacent major retinal vessels. The density of trapped leukocytes was calculated by dividing the number of static leukocytes (recognized as fluorescent dots) by the area of the observation region (in pixels). The density of static leukocytes was calculated in 8–10 peripapillary observation areas and an average density ($\times 10^{-5}$ cells/pixel$^2$) was obtained.

Blood pressures and heart rates were measured using a noninvasive cuff sensor and monitoring system (Ueda Electronics, Tokyo, Japan). Blood anticoagulated with EDTA was drawn from the abdominal aorta of each rat after the experiment to determine the leukocyte count using a hematology analyzer. The leukocyte count was determined using a hematology analyzer.

Statistical Analysis

All results are expressed as means±SD. The data were compared by analysis of variance (ANOVA) with post-hoc comparisons tested using Fisher's protected least significant difference (PLSD) procedure. Differences were considered statistically significant when p values were less than 0.05.

Results

Neutrophil CD11a, CD11b, and CD18 surface integrin levels were 62% (n=5, p=0.006), 54% (n=5, p=0.045) and 38% (n=5, p0.009) greater in diabetic vs. non-diabetic animals, respectively. Seventy-five percent more neutrophils from diabetic vs. non-diabetic animals adhered to rat endothelial cell monolayers (n=6, p=0.02). Pre-treatment of leukocytes with either anti-CD11b or anti-CD18 antibodies lowered the proportion of adherent diabetic neutrophils by 41% (n=6, p=0. 01 for each treatment), while anti-CD11a antibodies had no significant effect (n=6, p=0.5). In vivo, systemic administration of anti-CD18F(ab ')$_2$ fragments decreased diabetic retinal leukostasis by 62% (n=5, p=0.001).

Increased Surface Integrin Expression on Diabetic Neutrophils

Integrin expression was measured on the surface of neutrophils from normal and diabetic rats. As shown in Table 2, the flow cytometric analyses demonstrated statistically significant increases in the diabetic leukocyte CD11a, CD11b, and CD18 levels, as evidenced by the increases in mean channel fluorescence. Neutrophil CD11a, CD11b, and CD18 levels were 62% (n=5, p0.006), 54% (n=5, p0.045), and 38% (n=5, p=0.009) greater, respectively, on the one week-diabetic leukocytes vs. the non-diabetic leukocytes. Integrin expression was similarly increased on two week-diabetic neutrophils with CD11a, CD11b, and CD18 levels being 53%, 24%, and 38% greater, respectively.

TABLE 2

Flow-cytometric analysis of integrin molecule expression on neutrophils.

| | Control | Diabetes | Diabetes + control F(ab;)$_2$ | Diabetes + anti-CD18 F(ab')$_2$ |
|---|---|---|---|---|
| n | 5 | 5 | 5 | 5 |
| Body Weight | 268 ± 10 | 236 ± 4* | 233 ± 7* | 237 ± 17* |

TABLE 2-continued

Flow-cytometric analysis of integrin molecule expression on neutrophils.

|  | Control | Diabetes | Diabetes + control F(ab;)$_2$ | Diabetes + anti-CD18 F(ab')$_2$ |
|---|---|---|---|---|
| (g) |  |  |  |  |
| Plasma glucose (mg/dl) | 122 ± 21 | 327 ± 40* | 357 ± 60* | 351 ± 28* |
| Blood pressure (mmHg) | 110 ± 7 | 106 ± 13 | 103 ± 8 | 103 ± 7 |
| Leukocyte count (× 10$^3$ µL) | 6.4 ± 1.4 | 4.9 ± 1.6† | 5.0 ± 1.3 | 6.7 ± 0.9 |

Values are means ± SD.
*P<0.001 vs. control rats
†P<0.05 vs. anti-CD18 F(ab')$^2$-treated diabetic rats.

Figure 7:
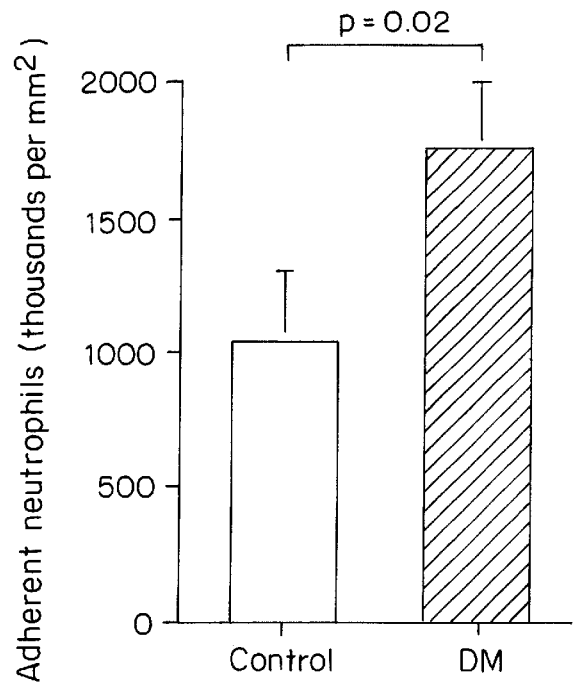
FIG. 7 is a bar graph showing the amount of adherent neutrophils to endothelium in vitro (thousands per mm$^2$) from control rats and rats having Diabetes Mellitus (DM). All data shown are means±Standard Deviation (SD).

Diabetic neutrophils exhibit increased adhesion to TNFα-activated endothelial cell monolayers in vitro The functional adhesion of purified neutrophils to cultured endothelial cell monolayers was investigated. Adhesion assays were performed by adding diabetic or non-diabetic neutrophils to TNF-α-stimulated rat endothelial cell monolayers under static conditions. TNF-α was added to maximize endothelial cell ICAM-1 expression. Preliminary experiments demonstrated a 2.7-fold increase in endothelial cell ICAM-1 expression with TNF-α (n=4, p<0.0001). FIG. 7 shows that adhesion of control and diabetic rat neutrophils to confluent TNF-activated rat endothelial cell monolayers under static conditions. Neutrophils isolated from diabetic rats demonstrated significantly increased adhesion to rat endothelial cell monolayers. FIG. 7 shows that adhesion of control and diabetic rat neutrophils to confluent TNF-activated rat endothelial cell monolayers under static conditions. Neutrophils isolated from diabetic rats demonstrated significantly increased adhesion to rat endothelial cell monolayers. As shown in FIG. 7, 75% more neutrophils from the diabetic rats adhered to the endothelial cell monolayers than neutrophils isolated from non-diabetic rats (n=6, p=0.02).

Figure 8:
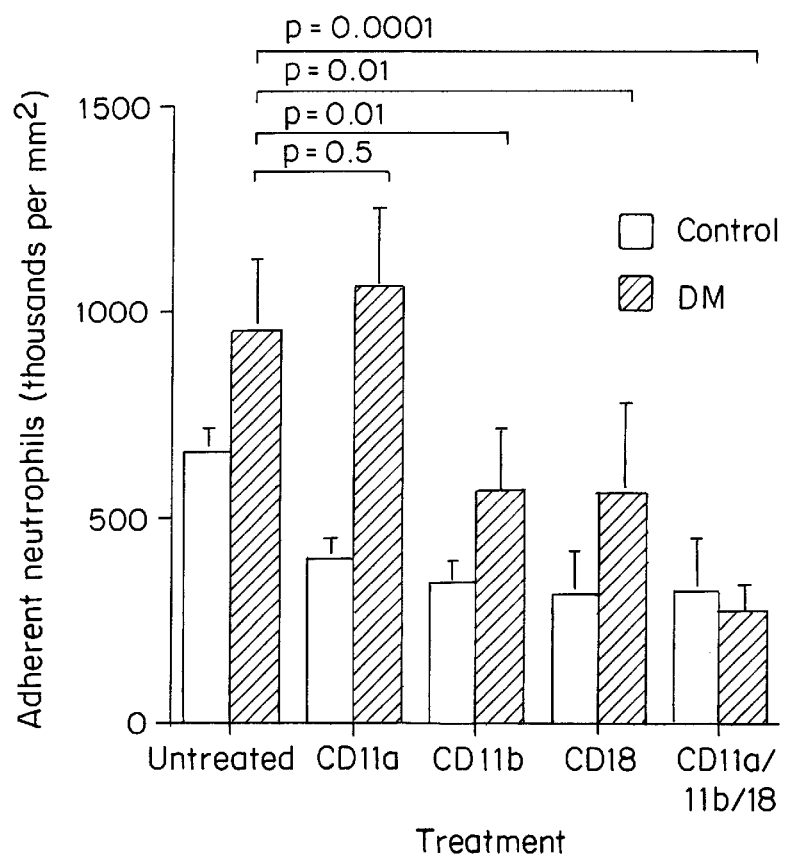
FIG. 8 is a bar graph showing the amount of adherent neutrophils (thousands per mm$^2$) for untreated, CD11a, CD11b, CD18, or CD11a/CD11b/CD18 cocktail treated for control and DM rats. All data shown are means±SD.
Figure 9A:
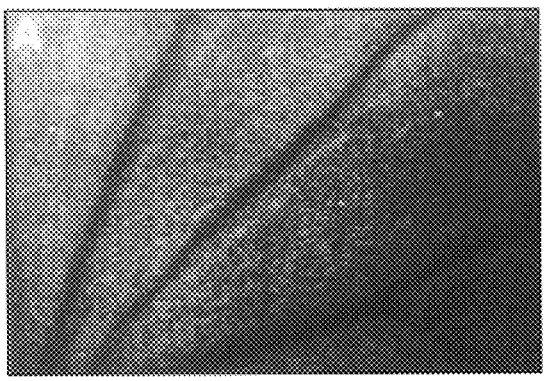
FIGS. 9A–D are photographs of leukostasis in from AOLF retinas in non-diabetic rat (FIG. 9A), diabetic rat (FIG. 9B), diabetic rat treated with the control F(ab')$_2$ (FIG. 9C) and anti-CD18 F(ab')$_2$ fragments treated rats (FIG. 9D).
Figure 9B:
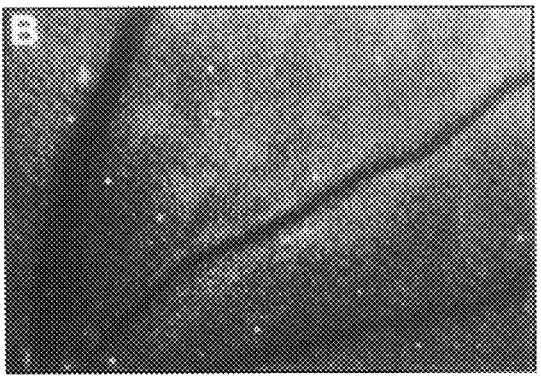
Figure 9C:
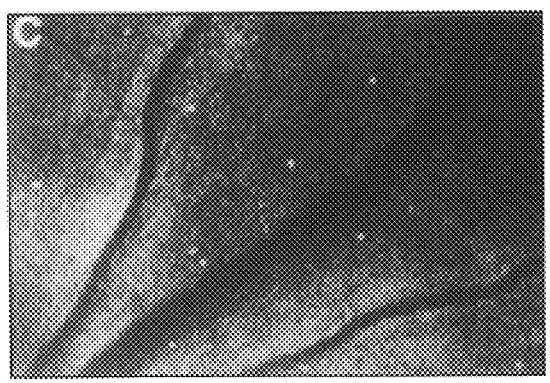
Figure 9D:
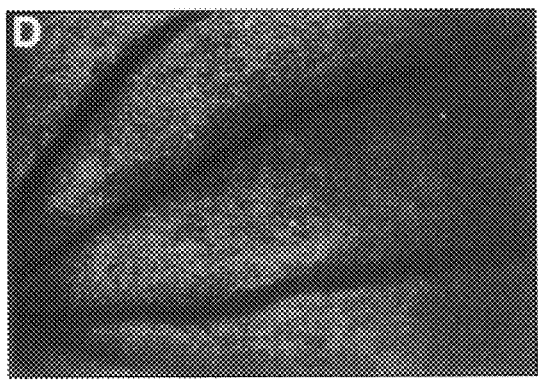

The $\beta_2$-integrin molecules mediating neutrophil adhesion in vitro were examined. FIG. 8 shows the effect of anti-integrin antibodies on neutrophil adhesion in vitro. Neutrophils were pre-incubated with anti-CD11a, anti-CD11b, anti-CD18 (30 µg/ml of each mAb), or an equimolar mixture of anti-CD11a/CD11b/CD18 antibodies prior to their use in the adhesion studies. In a representative experiment shown in FIG. 8, untreated diabetic neutrophils exhibited increased adhesion to TNFα-activated endothelial cell monolayers under all treatment conditions. Pretreatment with anti-CD11b or anti-CD18 antibodies each decreased diabetic neutrophil adhesion by 41% (n=6, p=0.01 for each treatment). In contrast, pretreatment with the anti-CD11a antibody did not significantly affect diabetic neutrophil adhesion (n=6, p=0.5 vs. untreated diabetic neutrophils). Moreover, treatment with an equimolar mixture of anti-CD11a, anti-CD11b, and anti-CD18 monoclonal antibodies significantly reduced diabetic neutrophil adhesion by 72% (n=6, p<0.0001 vs. untreated diabetic neutrophils). Non-diabetic neutrophil adhesion was also reduced with the anti-CD11a, anti-CD11b and anti-CD18 antibodies, as well as with the anti-CD11a/CD11b/CD18 antibody cocktail. The decreases were 39%, 49%, 53%, and 52%, respectively (n=6, p<0.05 for each treatment vs. untreated non-diabetic neutrophils).

In vivo CD18 Blockade Decreases Leukostasis in Diabetic Rat Retinas

Retinal leukostasis in living animals was measured with AOLF. Intravenous injection of acridine orange causes leukocytes and endothelial cells to fluoresce through the non-covalent binding of the molecule to double stranded DNA. When a scanning laser ophthalmoscope is utilized, retinal leukocytes within blood vessels can be visualized in vivo. Twenty minutes after acridine orange injection, static leukocytes in the capillary bed can be observed as fluorescent dots. These labeled cells are leukocytes because blocking CD18, expressed on leukocytes but not on endothelial cells, causes them to disappear (see below).

Leukocyte dynamics in the retina were observed after CD18 F(ab')$_2$ blockade as shown in the representative photos of FIG. 9. FIG. 9 shows retinal leukostasis following CD18 blockade. Representative photos from acridine orange leukocyte fluorography revealed static fluorescent leukocytes in the retinas of control and diabetic rats. The leukostasis in non-diabetic rat retina (FIG. 9A), was increased in diabetic rat retina (FIG. 9B), and unchanged following treatment with the control F(ab')$_2$ (FIG. 9C), however retinal leukostasis was reduced in diabetic rats treated with anti-CD 18 F(ab')$_2$ fragments (FIG. 9D). As expected, retinal leukostasis was increased in the diabetic vs. non-diabetic rat retinae (FIG. 9B vs. 9A). Treatment of the diabetic rats with the isotype control F(ab')2 fragments did not lead to detectable changes in the degree of leukostasis (FIG. 9C vs. 9B). However, treatment with the anti-CD18 F(ab')$_2$ fragments led to a striking decrease in retinal leukostasis (FIG. 9D vs. 9C).

Figure 10:
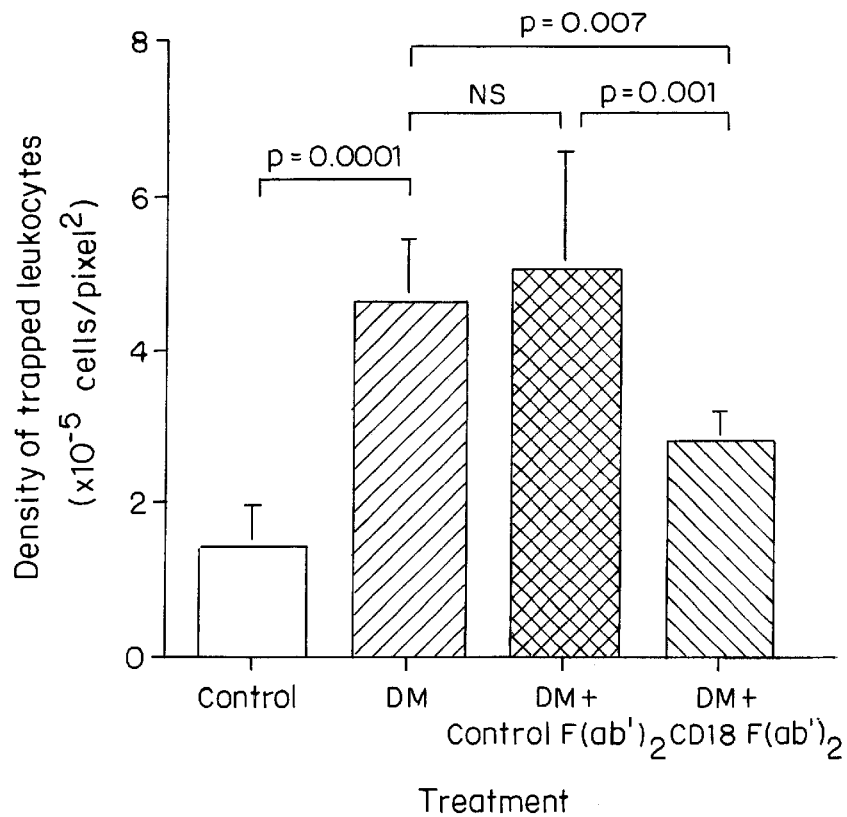
FIG. 10 is a bar graph showing the density of trapped leukocytes ($\times 10^{-5}$ cells/pixel$^2$) for control, DM, DM and F(ab')$_2$, and DM and anti-CD18 F(ab')$_2$ fragment treated rats.

Measurements of leukostasis were obtained throughout the entire retinae to avoid any potential sampling error and the means and standard deviations from independent experiments were compared (FIG. 10). FIG. 10 shows the quantitation of retinal leukostasis following CD18 blockade. When CD18 bioactivity was inhibited via systemic administration of 5 mg/kg of the anti-CD18 neutralizing F(ab')$_2$ (clone WT.3), retinal leukostasis was inhibited in diabetic rat retinas. This confnmed that anti-CD18 blockade significantly decreased leukostasis in diabetic rats by 62% (n=5, p=0.001 vs. animals receiving control F(ab')$_2$) (FIG. 10). The body weight, plasma glucose level, blood pressure, and leukocyte counts for the control and diabetic animals are shown in Table 3. The diabetic animals all had significantly elevated blood glucose levels and decreased body weight as compared with the normal rats, as is the norm. Blood pressure was similar among groups. The peripheral leukocyte counts in the diabetic anti-CD18 F(ab')2-treated animals were increased compared to the untreated diabetic animals, a result consistent with successful CD18 blockade.

TABLE 3

Characteristics of control, diabetic, control mAb treated diabetic, and anti-CD18 F(ab')$_2$-treated diabetic rats

|  | Control | Diabetes | p-value | n |
|---|---|---|---|---|
| CD11a | 115.0 ± 12.8 | 185.9 ± 18.5 | 0.006 | 5 |
| CD11b | 182.6 ± 39.2 | 281.9 ± 84.9 | 0.045 | 5 |
| CD18 | 193.2 ± 34.2 | 267.1 ± 34.3 | 0.009 | 5 |

Values are means ± SD of mean channel fluorescence.

The results of the blocking adhesion studies indicate that Mac-1 is the predominant CD18 integrin involved in diabetic neutrophil adhesion to activated RPEC monolayers. At present, the reason for a lack of a CD11a-dependent component in diabetic vs. non-diabetic neutrophil adhesion is not known. The residual non-CD18-dependent neutrophil adhesion may be due to the $VLA_4$-VCAM adhesion pathway because rat neutrophils constitutively express $VLA_4$ on their surface.

Conclusion: Neutrophils from diabetic animals exhibit higher levels of surface integrin expression and integrin-mediated adhesion. In vivo, CD18 blockade significantly decreases leukostasis in the diabetic retinal microvasculature. Integrin adhesion molecules serve as therapeutic targets for the treatment and/or prevention of early diabetic retinopathy.

EXAMPLE 3

Vascular Endothelial Growth Factor (VEGF)-Induced Retinal Vascular Permeability is Mediated by ICAM-1

Summary:

Two prominent VEGF-induced retinal effects are vascular permeability and capillary non-perfusion. The mechanisms by which these effects occur are not completely known. Using a rat model, it is shown that intravitreous injections of VEGF precipitate an extensive retinal leukocyte stasis (leukostasis) that coincides with enhanced vascular permeability and capillary non-perfusion. The leukostasis is accompanied by the upregulation of intercellular adhesion molecule-1 (ICAM-1) expression in the retina. The inhibition of ICAM-1 bioactivity with a neutralizing antibody prevents the permeability and leukostasis increases by 79% and 54%, respectively. These data are the first to demonstrate that a non-endothelial cell type contributes to VEGF-induced vascular permeability. Additionally, they identify a potential mechanism for VEGF-induced retinal capillary non-perfusion.

In experimental diabetes, the increased presence of static leukocytes in the retinal circulation is correlated with increased vascular permeability. The leukostasis and vascular permeability changes coincide with the upregulation of retinal ICAM-1. When ICAM-1 bioactivity is blocked with an antibody, retinal leukostasis and vascular permeability are reduced by 49% and 86%, respectively.

When the retina is bathed in pathophysiologic concentrations of vascular endothelial growth factor (VEGF), enhanced vascular permeability and capillary non-perfusion are among the vascular changes induced. The mechanisms by which these changes occur are largely unknown. The current studies examined the mechanisms underlying VEGF-induced retinal permeability and non-perfusion. Given the ability of VEGF to increase ICAM-1 expression in the retinal vasculature, the role of ICAM-1 in VEGF-induced vascular permeability and non-perfusion was examined in vivo.

Methods:

Animals. Long-Evans rats weighing approximately 200 g were used for these experiments. They were allowed free access to food and water in an air-conditioned room with a 12-hour light/12-hour dark cycle until they were used for the experiments. Intravitreous Injection Procedure. The rats were anesthetized with xylazine hydrochloride (4 mg/kg) (Phoenix Pharmaceutical, St. Joseph, Mo.) and ketamine hydrochloride (25 mg/kg) (Parke-Davis, Morris Plains, N.J.). Intravitreous injections were performed by inserting a 30-gauge needle into the vitreous at a site 1 mm posterior to the limbus of the eye. Insertion and infusion were performed and directly viewed through an operating microscope. Care was taken not to injure the lens or the retina. The head of the needle was positioned over the optic disc, and a 5 $\mu$l volume was slowly injected into the vitreous. Any eyes that exhibited damage to the lens or retina were discarded and not used for the analyses.

Acridine Orange Leukocyte Fluorography (AOLF) and Fluorescein Angiography. Leukocyte dynamics were evaluated using acridine orange leukocyte fluorography (AOLF). Nishiwaki H, et al., *Invest Ophthalmol Vis Sci*, 37:1341–1347 (1996); Miyamoto K, et al., *Invest Opthalmol Vis Sci*, 39:2190–2194 (1998). Intravenous injection of acridine orange causes leukocytes and endothelial cells to fluoresce through the non-covalent binding of the molecule to double stranded nucleic acid. When a scanning laser ophthalmoscope is utilized, retinal leukocytes and blood vessels can be visualized in vivo. Twenty minutes following acridine orange injection, static leukocytes in the capillary bed are observed.

Twenty-four hours before leukocyte dynamics were observed, a heparin-lock catheter was surgically implanted in the right jugular vein for the administration of acridine orange and sodium fluorescein dye. The catheter was subcutaneously externalized to the back of the neck. The rats were anesthetized for this procedure with xylazine hydrochloride (4 mg/kg) and ketamine hydrochloride (25 mg/kg).

Immediately before AOLF, each rat was again anesthetized, and the pupil of the left eye was dilated with 1% tropicamide (Alcon, Humancao, Puerto Rico) to observe leukocyte dynamics. A focused image of the peripapillary fundus of the left eye was obtained with a scanning laser ophthalmoscope (SLO; Rodenstock Instrument, Munich, Germany). Acridine orange (Sigma, St. Louis, Mo.) was dissolved in sterile saline (1.0 mg/ml) and 3 mg/kg was injected through the jugular vein catheter at a rate of 1 m/min. The fundus was observed with the SLO using the argon blue laser as the illumination source and the standard fluorescein angiography filter in the 40° field setting for 1 minute. Twenty minutes later, the fundus was again observed to evaluate retinal leukostasis. The images were recorded on videotape at the rate of 30 frames/sec. The recordings were analyzed on a computer equipped with a video digitizer (Radius, San Jose, Calif.) that digitizes video images in real time (30 frames/sec) at 640×480 pixels with an intensity resolution of 256 steps. For evaluating retinal leukostasis, an observation area around the optic disc measuring five disc diameters in radius was outlined by drawing a polygon bordered by the adjacent major retinal vessels. The area was measured in pixels and the density of trapped leukocytes was calculated by dividing the number of static leukocytes, which were recognized as fluorescent dots, by the area of the observation region. The density of leukocytes was calculated in eight peripapillary observation areas and an average density was obtained by averaging the eight density values.

Immediately after observing and recording the static leukocytes, fluorescein angiography was performed to study the relationship between static leukocytes and the retinal vasculature. Twenty $\mu$l of 1% sodium fluorescein was injected into the jugular vein catheter and the images were captured using the SLO as described above.

Quantitation of Retinal ICAM-1 mRNA Levels. Retinas were gently dissected free and cut at the optic disc immediately after enucleation and frozen in liquid nitrogen. Total RNA was isolated from rat retinas according to the acid guanidinium thiocyanate-phenol-chloroform extraction method. A 425-base pair EcoRi/BamrHI fragment of rat ICAM-1 cDNA was prepared by reverse transcription-polymerase chain reaction. The PCR product was cloned into pBluescript II KS vector. After linearization by digestion with EcoNI, transcription was performed with T7 RNA polymerase in the presence of [$^{32}$P]dUTP generating a 225-base pair riboprobe. An automated DNA sequencer verified the sequence of the cloned cDNA. Ten micrograms of total cellular RNA was used for the ribonuclease protection assay. All samples were simultaneously hybridized with an 18S riboprobe (Ambion, Austin, Tex.) to normalize for variations in loading and recovery of RNA. Protected fragments were separated on a gel of 5% acrylamide, 8M urea, 1x Tris-borate-EDTA, and quantified with a PhosphorImager (Molecular Dynamics, Sunnyvale, Calif.).

Quantitation of Retinal Vascular Permeability. Vascular leakage was quantified using the isotope dilution technique. Tilton RG, et al., *J. Clin Invest* 99:2192–2202 (1997). Briefly, purified monomer bovine serum albumin (BSA; Sigma, St. Louis, Mo.) (1 mg) was iodinated with 1 mCi of $^{131}$I or $^{125}$I using the iodogen method. Polyethylene tubing (0.58 mm internal diameter) was used to cannulate the right jugular vein and the left or right iliac artery. The tubing was filled with heparinized saline (400 U heparin/ml). The right jugular vein cannula was used for tracer injection. The iliac artery cannula was connected to a one ml syringe attached to a Harvard Bioscience model PHD 2000 constant withdrawal pump preset to withdraw at a constant rate of 0.055 ml/min. At time 0, [$^{125}$I]albumin (50 million cpm in 0.3 ml saline) was injected into the jugular vein and the withdrawal pump started. At the eight minute mark, 0.2 ml (50 million cpm in 0.3 ml saline) of [$^{131}$I]BSA was injected into the jugular vein. At the ten-minute mark, the heart was excised, the withdrawal pump was stopped, and the retina was quickly dissected and sampled for γ-spectrometry. Tissue and arterial samples were weighed and counted in a γ-spectrometer (Beckman 5500, Irvine, Calif.). The data were corrected for background and a quantitative index of [$^{125}$I]tissue clearance was calculated as previously described and expressed as μg plasma ×g tissue wet weight$^{-1}$×min$^{-1}$. Briefly, [$^{125}$I]BSA tissue activity was corrected for [$^{125}$I] BSA contained within the tissue vasculature by multiplying [$^{125}$I]BSA activity in the tissue by the ratio of [$^{125}$I]BSA/ [$^{131}$I]BSA in an arterial plasma sample. The vascular-corrected [$^{125}$I]BSA activity was divided by the time-averaged [$^{125}$I]BSA plasma activity (obtained from a well-mixed sample of plasma taken from the withdrawal syringe) and by the tracer circulation time (10 min) and then normalized per gram tissue wet weight.

Anti-ICAM-1 Antibody Inhibition of Retinal Vascular Permeability and Leukostasis. To study the iii vivo effect of ICAM-1 blockade on VEGF-induced retinal vascular permeability and leukostasis, a well characterized rat ICAM-1 neutralizing monoclonal antibody (mAb) was used utilized (IA29; R&D Systems, Minneapolis, Minn.). Tamatani T, et al., *Int Immunol*, 165–171 (1990); Kawasaki K, et al., *J. Immunol*, 150:1074–1083 (1993); Kelly K J, et al., *Proc Natl Acad Sci USA*, 91:812–816 (1994). The animals were randomly divided into five groups. The first group received no treatment. The second group received 5 μl of phosphate-buffered saline (PBS) injected into the vitreous of the left eye. The third group received 50 ng VEGF$_{165}$ in 5 μl PBS injected into the vitreous of the left eye (12.5 nM final concentration). The fourth group received 50 ng VEGF in PBS injected into the vitreous of the left eye plus 5 mg/kg isotype-matched normal mouse IgG1 (R&D Systems) given intravenously. The fifth group received 50 ng VEGF in PBS injected into the vitreous of the left eye plus 5 mg/kg of the anti-ICAM-1 mAb given intravenously. Twenty-four hours later, retinal leukocyte dynamics and vascular permeability were quantified.

Statistical Analysis. All results are expressed as the mean±SD. Unpaired groups of two were compared using the two sample t-test or the two sample t-test with Welch's correction. To compare three or more groups, analysis of variance (ANOVA) followed by the post hoc test with Fisher's protected least significant difference (PLSD) procedure was used. Differences were considered statistically significant when P values were less than 0.05.

Figure 12:
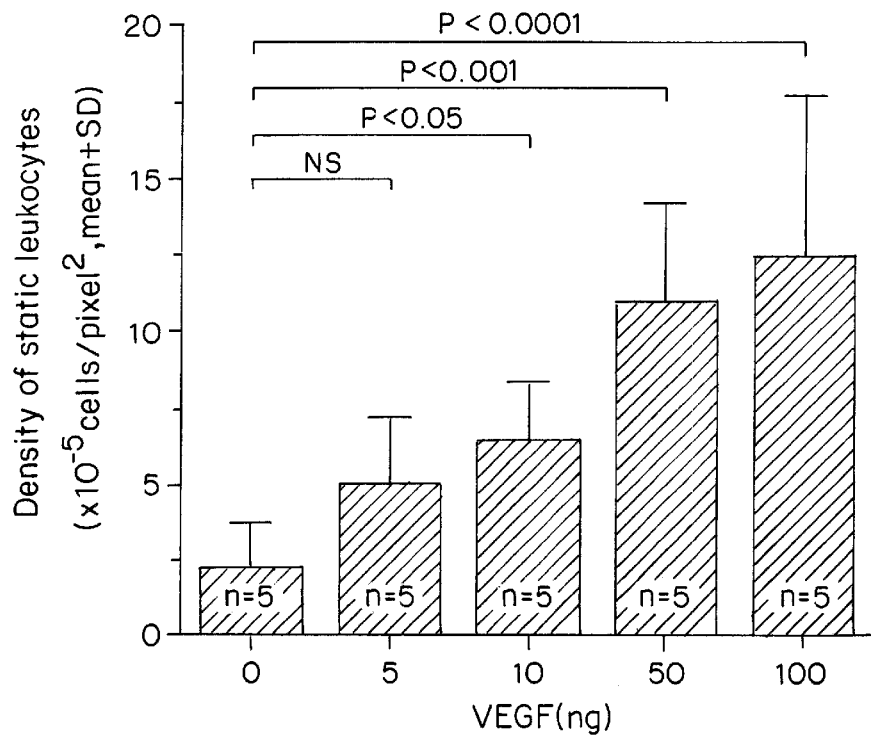
FIG. 12 is a bar graph showing the density of trapped leukocytes ($\times 10^{-5}$ cells/pixel$^2$, mean=SD) in the retina using AOLF for rats injected intravitreously with 0, 5, 10, 50, 100 ng of VEGF after 48 hours.
Figure 13:
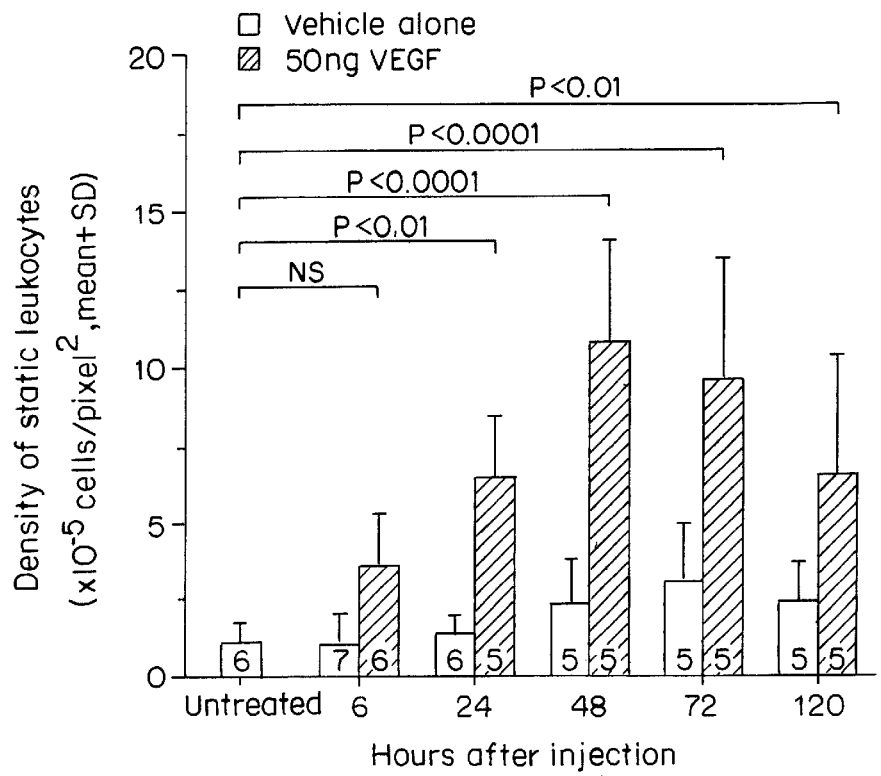
FIG. 13 is a bar graph showing the density of trapped leukocytes ($\times 10^{-5}$ cells/pixel$^2$, mean=SD) in the retina using AOLF for rats injected intravitreously with the vehicle alone or with 50 ng of VEGF after 6, 24, 48, 72, or 120 hours.

Results:

VEGF-induced Retinal Leukostasis. FIG. 11A shows AOLF appearance of a normal retinal prior to injection of 50 ng VEGF. FIG. 11B shows AOLF appearance of the same retinal area 48 h following intravitreous VEGF injection. Numerous static leukocytes are visible, as well as vessel dilation and tortuosity. A single 50 ng intravitreous injection of VEGF$_{65}$ (R& D Systems, Minneapolis, Minn.) in 5 μl PBS was able to induce marked retinal leukostasis 48 h later (FIG. 11). Vessel dilation and tortuosity were also evident. A dose-response study demonstrated that a 2.6-fold increase in leukostasis could be induced with as little as 10 ng VEGF (2.5 nM) (FIG. 12, n=5, p<0.05). A plateau was reached with 50–100 ng VEGF (~4–5-fold, n=5, p=<0.001 to 0.0001). Based on these data, the 50 ng dose was chosen for the time course experiments. Intravitreous injections of 50 ng VEGF were followed by AOLF 6, 24, 48, 72, and 120 h later. Twenty-four hours following intravitreous injection, VEGF increased retinal leukostasis 4.8-fold (FIG. 13, n=5, p<0.01 vs. vehicle control). The VEGF-induced leukostasis increases peaked 48 h post-injection and persisted for at least 120 h (n=5, p<0.01).

Figure 14:
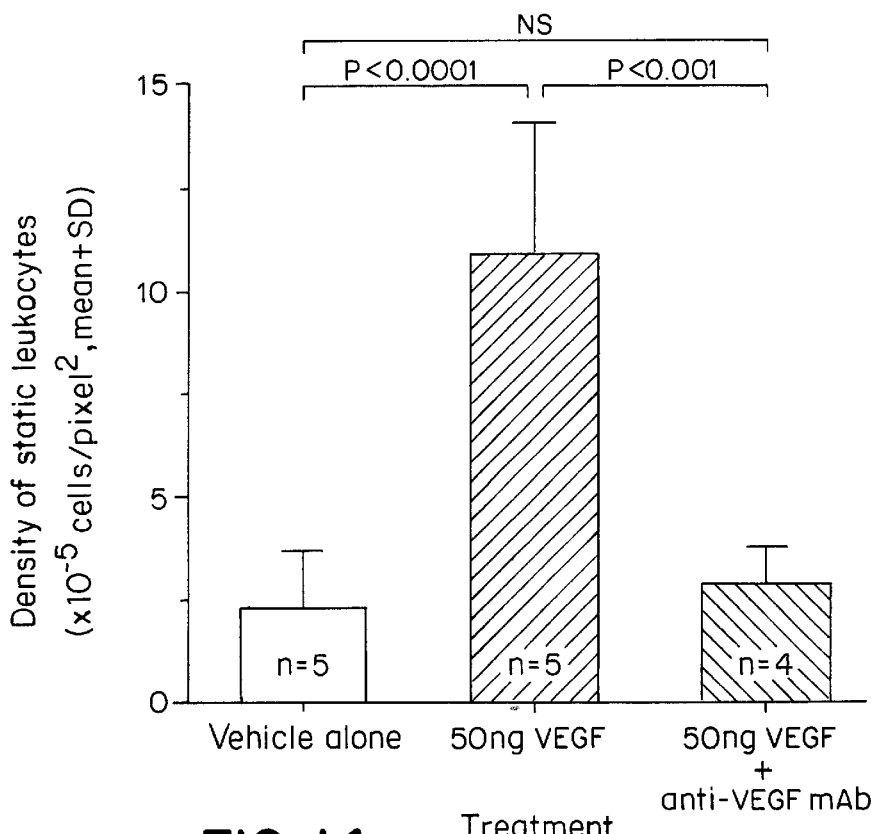
FIG. 14 is a bar graph showing the density of trapped leukocytes ($\times 10^{-5}$ cells/pixel$^2$, mean=SD) in the retina using AOLF for rats injected intravitreously with the vehicle alone or 50 ng of VEGF with and without anti-VEGF mAb treatment after 48 hours.

To confirm that this effect was due to VEGF alone, four rats received a mixture of VEGF with a 50:1 molar excess of a previously characterized VEGF neutralizing monoclonal antibody (A4.6.1, Genentech, South San Francisco, Calif.) (FIG. 14). Co-injection of the anti-VEGF antibody completely abrogated the VEGF-induced leukostasis 48 h later (n=4, p<0.001).

VEGF-induced Retinal Capillary Perfusion. FIG. 15 shows leukocyte-induced capillary non-perfiusion. FIG. 15A shows the retina 48 hours after fifty ng VEGF was delivered via intravitreous injection as measured with AOLF. AOLF was immediately followed by fluorescein angiography and FIG. 15B shows areas of capillary non-perfusion downstream from static leukocytes. Fluorescein angiography performed 20 minutes following AOLF revealed relatively large areas of downstream capillary non-perfusion associated with some of the static leukocytes (FIG. 15). The majority of the leukocytes observed appeared to be in the intravascular space. Normal and vehicle injected eyes did not exhibit non-perfusion.

Figure 16A:
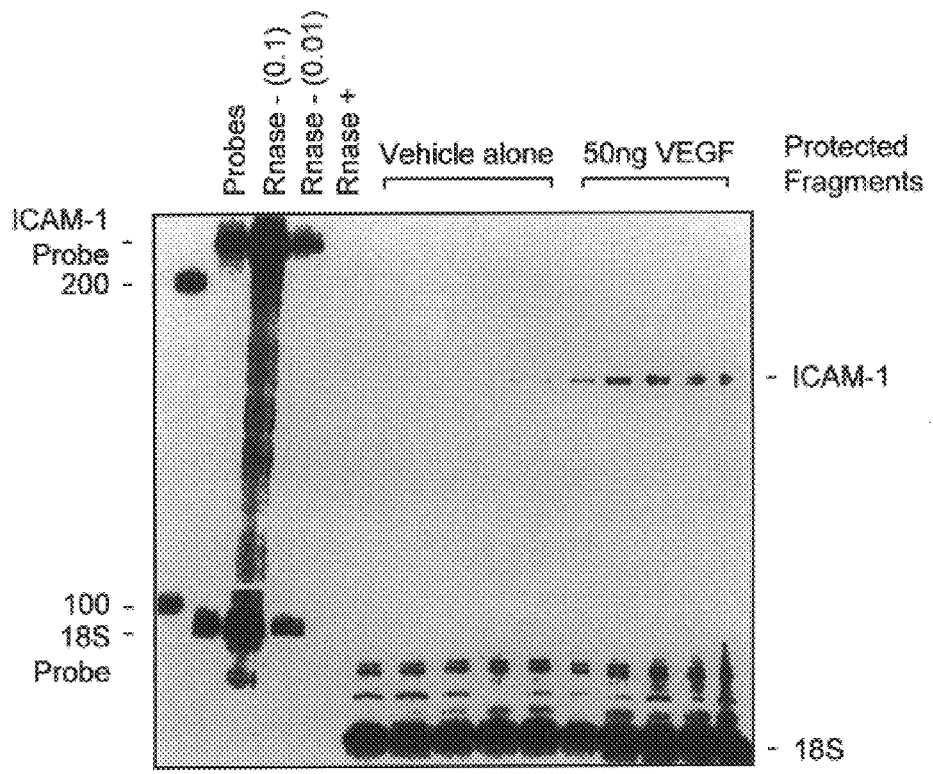
FIGS. 16A–B show VEGF-induced retinal ICAM-1 gen expression.
Figure 16B:
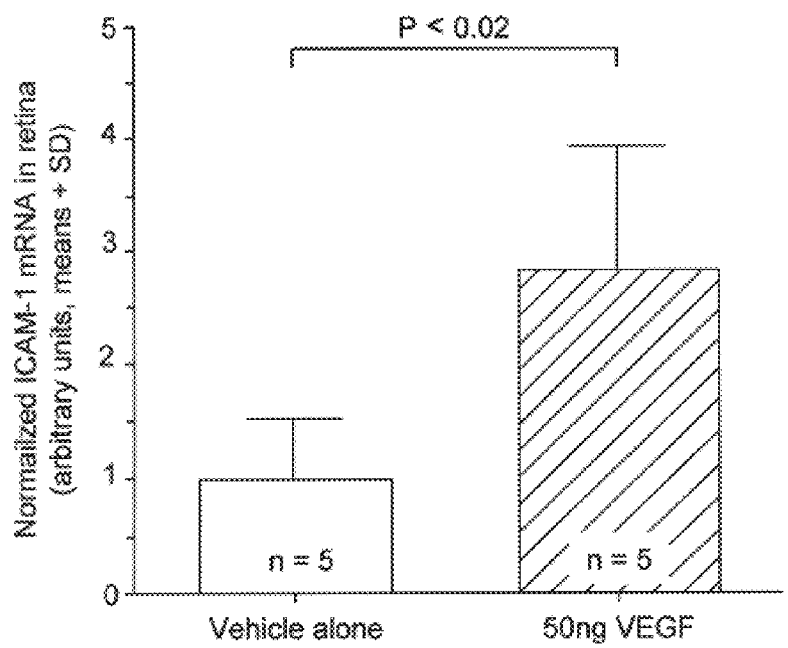

VEGF-induced Retinal ICAM-1 Gene Expression. Twenty hours following intravitreous injection of 50 ng VEGF or PBS vehicle alone, total RNA was isolated from each rat retina and ICAM-1 gene expression was quantitated using the ribonuclease protection assay (FIG. 16A). When normalized to 18S, retinal ICAM-1 levels in the VEGF-injected eyes were 2.8-fold greater than in the eyes injected with vehicle alone (FIG. 16B, n=5, p<0.02).

Figure 17A:
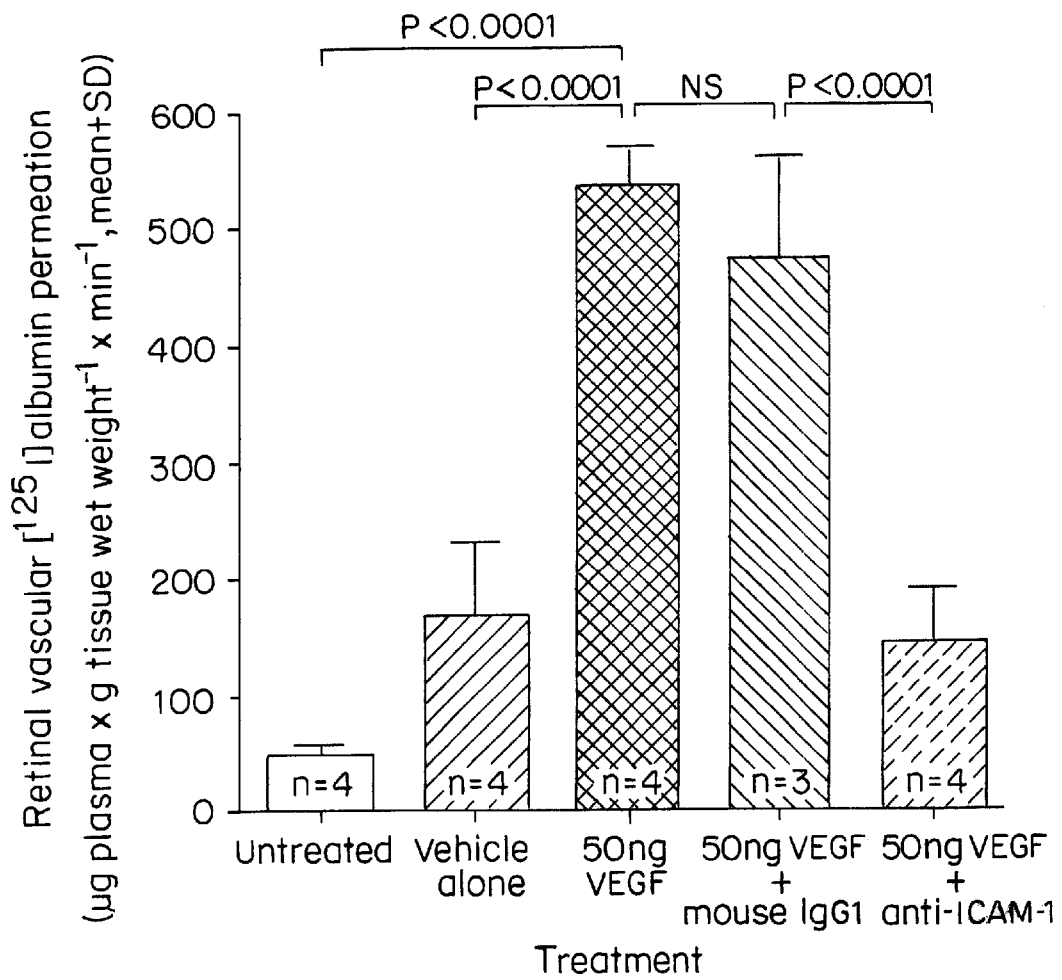
FIGS. 17A–B are bar graphs showing the effect of anti-ICAM-1 mAb on permeability and leukostasis following intravitreous VEGF injection.
Figure 17B:
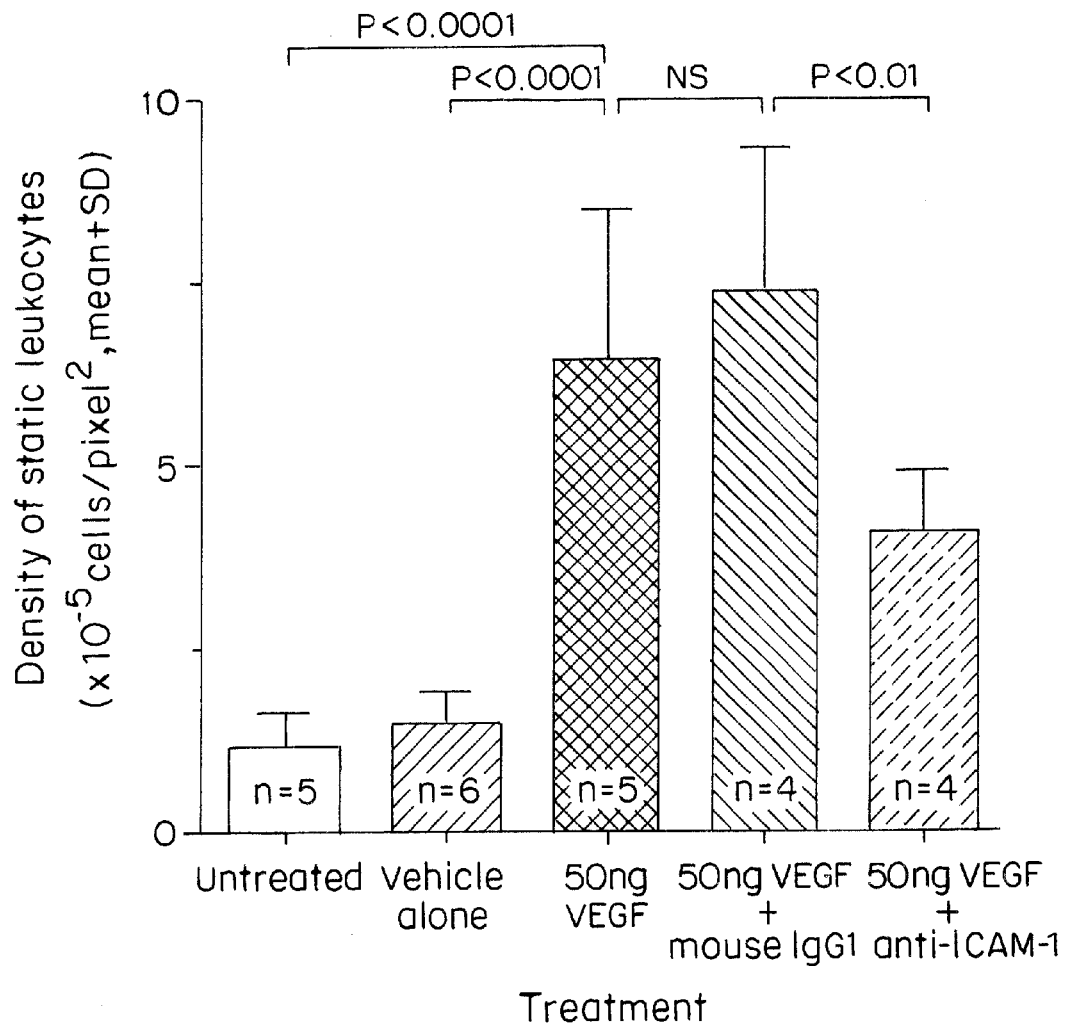

ICAM-1 Blockade of VEGF-induced Vascular Permeability and Leukostasis. Animals receiving intravitreous VEGF had a 3.2-fold increase in vascular permeability 24 h following injection (FIG. 17A, n=4, p<0.0001 vs. vehicle control). Similarly, there was a 4.3-fold increase in retinal leukostasis (FIG. 17B, n=5, p<0.0001 vs. vehicle control). Intravenous treatment with the non-immune control antibody did not significantly alter the degree of VEGF-induced permeability (FIG. 17A, n=3, p>0.05) or leukostasis (FIG. 17B, n=4, p>0.05). However, the animals receiving intravenous anti-ICAM mAb had a 79% reduction in VEGF-induced retinal vascular permeability (FIG. 17A, n=4, p<0.0001 vs. untreated) and a 54% reduction in VEGF-induced retinal leukostasis (FIG. 17B, n=4, p<0.01 vs. untreated).

EXAMPLE 4

CD18 and ICAM-1 Dependent Corneal Neovascularization and Inflammation Following Limbal Injury Materials and Methods Corneal Neovascularization Model Male CD18-deficient and ICAM-1 -deficient mice were used (Jackson Labs, Bar Harbor, Me.) and strain-specific normal male C57BL/6 mice served as controls. The mice were anesthetized with 50 mg/kg intraperitoneal pentobarbital sodium and a drop of proparicaine was instilled into the left eye. A number 15 Bard-Parker blade (vendor and city) was used to debride the corneal epithelium. Two microliters of 0.15 M NaOH was then applied topically and the limbal epithelium was removed with a Tooke Corneal Knife, 2.5–15 mm Dissecting Blade (Arista, N.Y.) A rotary motion parallel to limbus was utilized. Erythromycin ophthalmic ointment was instilled postoperatively.

Measurement of Corneal Neovascularization

For measurement of neovascularization, mice were injected approximately 8 μg of the endothelial cell-specific marker BS-1 lectin conjugated to FITC (Vector Laboratory) per 1 g of body weight on day 7 after scraping or day 2 after implantation of VEGF. In 30 minutes after the injection of the dye, the eyes were harvested and fixed with 10% neutral buffered formalin, and then the cornea was flat-mounted on slide glasses. Fluorescence in the flat-mounted cornea was captured using CCD camera attached to a Leica Fluorescence microscope and saved to Macintosh 6500 (Apple computer) as a .tif image file. The images were taken with the same settings including exposure time on both study group and control one. The digital images were processed using OpenLab Software and integrated optical density in the images was measured.

Peripheral Leukocyte Counts

Peripheral blood samples were collected from tail vessels into Eppendorf tube with EDTA when cornea that was served for confirming infiltration of PMN was enucleated. For total leukocyte count blood was incubated with Turk solution and then counted manually using Hemocytemeter. The preparation of a thin, air-dried edge smear was made to perform the microscopic manual differential and stained with Giemsa solution. PMN count was then calculated from the differential.

Corneal Leukocyte Counts

To determine the counts of PMN infiltration in cornea the eyes were enucleated on day 2 after scraping or implantation of VEGF, and stored in 10% neutral buffered formalin. The tissue was embedded in paraffin, and 5-μm-thick sections were cut and then transferred to slide glasses. The tissue sections were stained with Giemsa stain. The slides were then observed microscopically, and the number of PMNs was counted in 5 fields (2 of periphery, 2 of midperiphery and 1 of center) in the cornea from inflammatory models and in 1 field between VEGF pellet and corneal limbus in the cornea from VEGF-induced Neovascularization models.

Statistical Analysis Student t-test and ANOVA were used for the comparison. Probability less than 0.05 was considered significant.

Results:

Corneal Neovascularization in CD18 KO, ICAM-1 KO and Normal Mice

To determine if CD18 and ICAM-1 were important in the development of the corneal neovascularization associated with limbal injury, limbal injury was followed by uantitation of corneal neovascularization 7 d later. Compared to the strain-specific controls, the CD18 null mice 39% fewer vessels (n=5, p=0.0054). Similarly, the ICAM-1 null mice has 33% less neovascularization that the control mice (n=5, p=0.013).

Corneal PMN Density in CD18 KO, ICAM-1 KO and Normal Mice

To determine if the inhibition of corneal neovascularization was associated with the decreased transmigration of PMN into the cornea, corneal PMN counts were performed 2 d following limbal injury. This time point was chosen because it manifested maximum corneal opacity and corneal leukocyte infiltration. Compared to the strain-specific controls, the CD null mice had 66% fewer PMN (n=5, p=0.0016). The ICAM-1 null mice had 65% fewer PMN (n=5, p=0.0019) compared to the strain-specific controls.

Peripheral Blood PMN Counts in CD18 KO, ICAM-1 KO and Normal Mice

To determine if peripheral PMN cell counts were altered in the animals, standard PMN counts were calculated from the differential. The average count in the C57BL6/J controls was 6263±2313.18 vs. counts of 9315±1486 and 10,794±2199 in the CD18 and ICAM knockout mice, respectively.

Discussion:

The data indicate that CD18 and ICAM-1 amplify the corneal neovascularization that occurs following limbal injury. The process is associated with higher corneal leukocyte counts, and the latter are likely causal, in part, for the increased neovascularization. The data also indicate that the CD18 and ICAM-1 KO mice have a higher proportion of circulating leukocytes, a result consistent with absence of CD18 and ICAM-1 systemically. It also confirms that the corneal leukocytes likely transmigrated, and are not the result of systemic leukocytopenia. Taken together, these data identify CD18 and ICAM-1 mediators of the inflammatory corneal neovascularization in a clinically relevant model of limbal injury.

Experiments described herein show that limbal injury upregulates VEGF. When VEGF is inhibited, corneal neovascularization is reduced. VEGF is known to act directly on the endothelial cells and the vasculature, resulting in neovascularization. However, leukocytes augment this process. The mechanism involves VEGF. Leukocytes, via their own VEGF, serve to amplify the direct effects of non-leukocyte VEGF on the vasculature. VEGF has been demonstrated in neutrophils, monocytes, eosinophils, lymphocytes and platelets. It has also been identified in the neutrophils and monocytes that infiltrate the cornea following limbal injury. The fact that some leukocytes possess high affinity VEGF receptors and migrate in response to VEGF is consistent with this scenario. Endogenous VEGF triggers leukocyte adhesion, transmigration and further VEGF release, producing a positive feedback loop.

Equivalents

While this invention has been particularly shown and described with references to preferred embodiments thereof, it will be understood by those skilled in the art that various changes in form and details may be made therein without departing from the spirit and scope of the invention as defined by the appended claims.

The relevant teachings of all the references, patents and/or patent applications cited herein are incorporated herein by reference in their entirety.

What is claimed is:

1. A method for reducing retinal injury in a mammal, wherein the injury involves retinal edema or retinal ischemia, comprising administering to the mammal an antibody or antibody functional fragment that is specific for CD18, CD11a, or CD11b and inhibits the binding of a leukocyte to an endothelial cell or to another leukocyte, wherein a reduction in retinal edema or retinal ischemia occurs.

2. A method for reducing retinal injury in a mammal, comprising administering to the mammal an antibody or antibody functional fragment, wherein the antibody or antibody functional fragment is specific for CD18, CD11a, or CD11b, thereby a reducing retinal injury.

3. The method of claim 2, wherein the antibody or antibody functional fragment is administered in a pharmaceutically acceptable carrier.

4. A method for treating an individual having retinal injury, wherein the injury is associated with retinal edema and/or retinal ischemia, comprising administering to the individual an antibody or antibody functional fragment that is specific for CD18, CD11a, or CD11b, wherein a reduction in retinal edema and/or retinal ischemia occurs.

5. The method of claim 4, wherein the decrease of ischemia and/or edema is between about 10% and about 90%.

6. The method of claim 4, wherein the individual has diabetic retinopathy.

7. A method for treating an individual having diabetic retinopathy comprising administering to the individual a CD18, CD11a and/or CD11b antibody or antibody functional fragment, wherein the CD18, CD11a and/or CD11b antibody or antibody functional fragment inhibits leukocyte interaction.

8. The method of claim 7, wherein a decrease of ischemia and/or edema occurs.

9. The method of claim 8, wherein the decrease of ischemia and/or edema is between about 10% and about 90%.

10. A method for treating an individual with retinal edema comprising administering to the individual a CD18, CD11a and/or CD11b antibody or antibody functional fragment, wherein a decrease in the retinal edema occurs.

11. The method of claim 10, wherein the decrease of edema is between about 10% and about 90%.

12. A method for treating an individual with retinal ischemia comprising administering to the individual a CD18, CD11a and/or CD11b antibody or antibody functional fragment, wherein a decrease in ischemia occurs.

13. The method of claim 12, wherein the decrease of ischemia is between about 10% and about 90%.

14. A method for of reducing retinal leukostasis in a mammal comprising administering to the mammal an effective amount of a CD18, CD11a and/or CD11b antibody or antibody functional fragment.

15. The method of claim 14, wherein retinal leukostasis is reduced by between about 10% and 90%.

16. A method of decreasing retinal leukocyte adhesion in a mammal, comprising administering to the mammal an effective amount of an antibody or antibody functional fragment that is specific for CD11a, CD11b, CD18 or a combination thereof.

17. The method of claim 16, wherein retinal leukocyte adhesion is decreased between about 10% and 90%.

18. A method for reducing retinal injury in a mammal, wherein the injury involves retinal edema or retinal ischemia, comprising administering to an eye of the mammal an antibody or antibody functional fragment that is specific for CD18, CD11a, or CD11b and inhibits the binding of a leukocyte to an endothelial cell or to another leukocyte, wherein a reduction in retinal edema or retinal ischemia occurs.

19. A method for reducing retinal injury in a mammal, comprising administering to an eye of the mammal an antibody or antibody functional fragment, wherein the antibody or antibody functional fragment is specific for CD18, CD11a, or CD11b, thereby reducing retinal injury.

20. A method for treating an individual having retinal injury, wherein the injury is associated with retinal edema and/or retinal ischemia, comprising administering to an eye of the individual an antibody or antibody functional fragment that inhibits CD18, CD11b cud/or CD11a, wherein a reduction in retinal edema and/or retinal ischemia occurs.

21. A method for treating an individual having diabetic retinopathy comprising administering to an eye of the individual a CD18, CD11a and/or CD11b antibody or antibody functional fragment, wherein the CD18, CD11a and/or CD11b antibody or antibody functional fragment inhibits leukocyte interaction.

22. A method for treating an individual with retinal edema comprising administering to an eye of the individual a CD18, CD11a and/or CD11b antibody or antibody functional fragment, wherein a decrease in the retinal edema occurs.

23. A method for treating an individual with retinal ischemia comprising administering to an eye of the individual a CD18, CD11a and/or CD11b antibody or antibody functional fragment, wherein a decrease in ischemia occurs.

24. A method of treating diabetic retinopathy in an individual, comprising administering to an eye of the individual a CD18, CD11a and/or CD11b antibody or antibody functional fragment and at least one additional antagonist that inhibits the binding of a leukocyte to an endothelial cell or to another leukocyte.

25. A method of reducing retinal leukostasis an a mammal comprising administering to an eye of the mammal an effective amount of a CD18, CD11a and/or CD11b antibody or antibody functional fragment.

26. A method of decreasing retinal leukocyte adhesion in a mammal, comprising administering to an eye of the mammal an effective amount of an antibody or antibody functional fragment that is specific for CD11a, CD11b, CD18 or a combination thereof.

* * * * *

UNITED STATES PATENT AND TRADEMARK OFFICE
CERTIFICATE OF CORRECTION

PATENT NO. : 6,524,581 B1  Page 1 of 1
DATED : February 25, 2003
INVENTOR(S) : Anthony P. Adamis It is certified that error appears in the above-identified patent and that said Letters Patent is hereby corrected as shown below:

Column 35,
Line 55, delete "for";
Line 26, delete "cud/or" and insert -- and/or --.

Signed and Sealed this

Fourteenth Day of October, 2003

JAMES E. ROGAN
*Director of the United States Patent and Trademark Office*